(12) United States Patent
Kim et al.

(10) Patent No.: US 11,905,245 B2
(45) Date of Patent: Feb. 20, 2024

(54) HETEROCYCLIC COMPOUND AND ORGANIC LIGHT EMITTING DEVICE COMPRISING THE SAME

(71) Applicant: LG Chem, Ltd., Seoul (KR)

(72) Inventors: Juhwan Kim, Daejeon (KR); Jaechol Lee, Daejeon (KR); Jaesoon Bae, Daejeon (KR); Soyoung Yu, Daejeon (KR); Young Kwang Kim, Daejeon (KR); Daeho Kim, Daejeon (KR)

(73) Assignee: LG Chem, Ltd. (KR)

( * ) Notice: Subject to any disclaimer, the term of this patent is extended or adjusted under 35 U.S.C. 154(b) by 621 days.

(21) Appl. No.: 17/260,395

(22) PCT Filed: Dec. 3, 2019

(86) PCT No.: PCT/KR2019/016947
§ 371 (c)(1),
(2) Date: Jan. 14, 2021

(87) PCT Pub. No.: WO2020/116904
PCT Pub. Date: Jun. 11, 2020

(65) Prior Publication Data
US 2021/0284607 A1    Sep. 16, 2021

(30) Foreign Application Priority Data
Dec. 3, 2018    (KR) .................. 10-2018-0153910
Dec. 2, 2019    (KR) .................. 10-2019-0158472

(51) Int. Cl.
*C07D 209/82*     (2006.01)
*H10K 85/40*      (2023.01)
(Continued)

(52) U.S. Cl.
CPC ......... *C07D 209/82* (2013.01); *C07D 215/04* (2013.01); *C07D 215/12* (2013.01);
(Continued)

(58) Field of Classification Search
CPC .. C07D 215/04; C07D 215/12; C07D 215/14; C07D 215/16; C07D 215/18;
(Continued)

(56) References Cited

U.S. PATENT DOCUMENTS

2004/0251816 A1    12/2004  Leo et al.
2014/0061614 A1*   3/2014   Sisk ................ H10K 85/654
                                                    546/256
(Continued)

FOREIGN PATENT DOCUMENTS

CN    101597259 A    12/2009
JP    2017075114 A    4/2017
(Continued)

OTHER PUBLICATIONS

Partial machine translation of KR-20130023071-A (obtained Sep. 7, 2023).*

(Continued)

*Primary Examiner* — Kregg T Brooks
(74) *Attorney, Agent, or Firm* — Lerner David LLP

(57) ABSTRACT

The present disclosure relates to a novel heterocyclic compound represented by the following Chemical Formula 1 and to an organic light emitting device comprising the same:

(Continued)

[Chemical Formula 1]

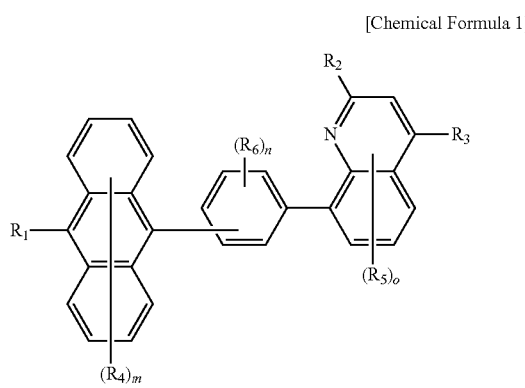

wherein, $R_1$, $R_2$, $R_3$, $R_4$, $R_5$, $R_6$, m, n and o are described herein.

9 Claims, 3 Drawing Sheets

(51) Int. Cl.
 *H10K 85/60* (2023.01)
 *C07D 215/04* (2006.01)
 *C07D 215/12* (2006.01)
 *H10K 50/11* (2023.01)
(52) U.S. Cl.
 CPC ........... *H10K 85/40* (2023.02); *H10K 85/615* (2023.02); *H10K 85/631* (2023.02); *H10K 85/6572* (2023.02); *H10K 50/11* (2023.02)

(58) Field of Classification Search
 CPC ............. C07D 215/38; C07C 2603/24; H10K 85/615; H10K 85/6572
 See application file for complete search history.

(56) References Cited

U.S. PATENT DOCUMENTS

| | | |
|---|---|---|
| 2015/0357574 A1 | 12/2015 | Ito et al. |
| 2016/0351816 A1 | 12/2016 | Kim et al. |
| 2016/0351818 A1 | 12/2016 | Kim et al. |
| 2017/0179402 A1 | 6/2017 | Kim et al. |

FOREIGN PATENT DOCUMENTS

| | | | |
|---|---|---|---|
| KR | 20000051826 A | | 8/2000 |
| KR | 20110049554 A | | 5/2011 |
| KR | 20110123701 A | | 11/2011 |
| KR | 20130023071 A | * | 3/2013 |
| KR | 20140058290 A | | 5/2014 |
| KR | 20140082437 A | | 7/2014 |
| KR | 20140090410 A | | 7/2014 |
| KR | 20140095726 A | | 8/2014 |
| KR | 20140095728 A | | 8/2014 |
| KR | 20140147743 A | | 12/2014 |
| KR | 20160141359 A | | 12/2016 |
| KR | 20160141360 A | | 12/2016 |
| KR | 20170075114 A | | 7/2017 |
| WO | 2003012890 A2 | | 2/2003 |
| WO | 2014204234 A1 | | 12/2014 |

OTHER PUBLICATIONS

International Search Report for PCT/KR2019/016947 dated Mar. 20, 2020; 3 pages.

* cited by examiner

[FIG. 1]
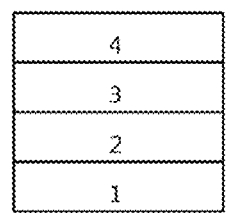
[FIG. 2]
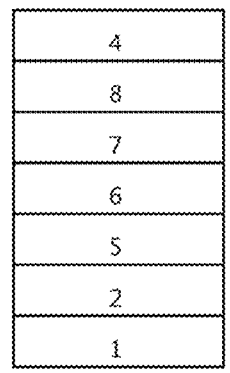
[FIG. 3]
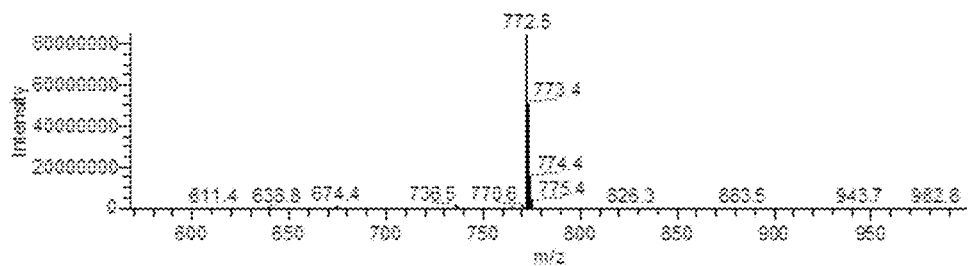

[FIG. 4]
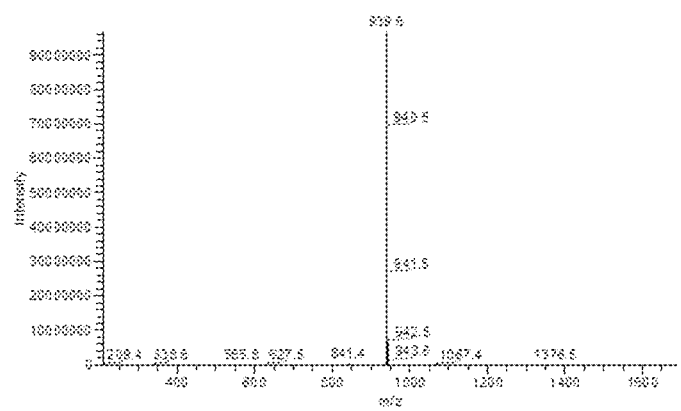
[FIG. 5]
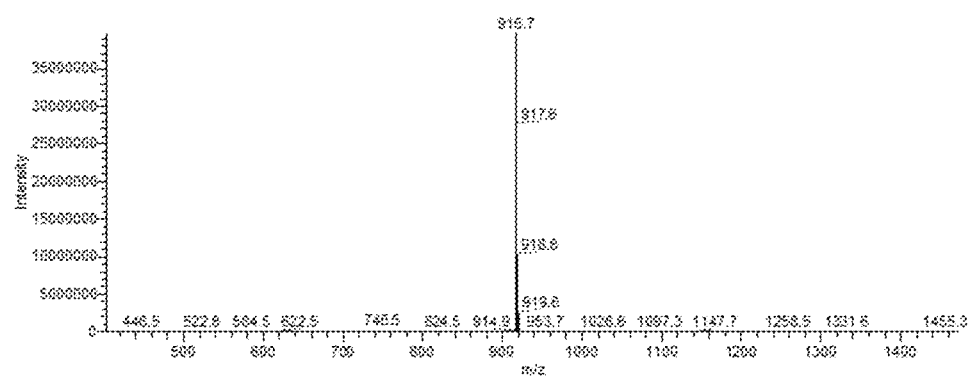

[FIG. 6]
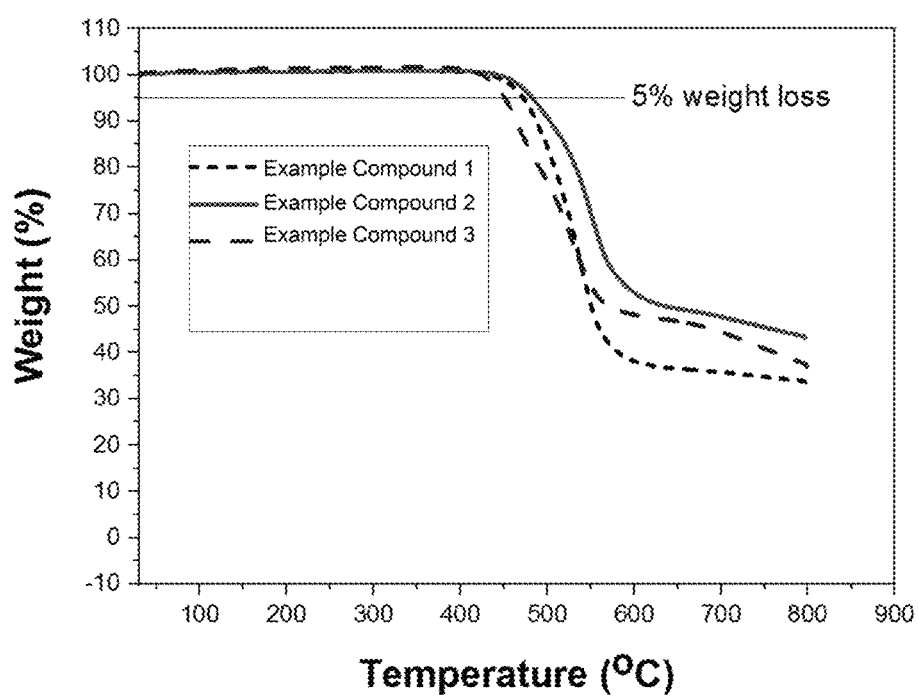

HETEROCYCLIC COMPOUND AND ORGANIC LIGHT EMITTING DEVICE COMPRISING THE SAME

CROSS-REFERENCE TO RELATED APPLICATION(S)

This application is a national phase entry under 35 U.S.C. § 371 of International Application No. PCT/KR2019/016947 filed Dec. 3, 2019, which claims priority from Korean Patent Application No. 10-2018-0153910 filed Dec. 3, 2018, and Korean Patent Application No. 10-2019-0158472 filed Dec. 2, 2019, all of which are incorporated herein by reference.

BACKGROUND OF THE INVENTION

(A) Field of the Invention

The present disclosure relates to a novel heterocyclic compound and an organic light emitting device comprising the same.

(B) Description of the Related Art

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

Meanwhile, recently, in order to reduce process costs, an organic light emitting device using a solution process, particularly an inkjet process, has been developed instead of a conventional deposition process. In the initial stage of development, attempts have been made to develop organic light emitting devices by coating all organic light emitting device layers by a solution process, but current technology has limitations. Therefore, only HIL, HTL, and EML are processed in a layer device structure by a solution process, and a hybrid process utilizing traditional deposition processes is being studied as a subsequent process.

In this regard, the present disclosure provides novel materials for organic light emitting devices that can be used for an organic light emitting device and simultaneously, can be deposited by a solution process.

PRIOR ART LITERATURE

Patent Literature (Patent Literature 0001) Korean Unexamined Patent Publication No. 10-2000-0051826

SUMMARY OF THE INVENTION

Technical Problem

It is an object of the present disclosure to provide a novel heterocyclic compound and an organic light emitting device.

Technical Solution

According to an aspect of the present disclosure, there is provided a compound represented by the following Chemical Formula 1:

[Chemical Formula 1]

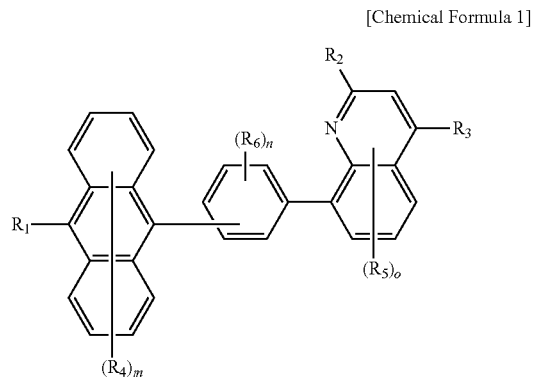

in the Chemical Formula 1.

$R_1$ is a substituted or unsubstituted $C_{6-60}$ aryl, $R_2$ and $R_3$ are each independently a substituted or unsubstituted $C_{3-10}$ cycloalkyl; a substituted or unsubstituted $C_{6-60}$ aryl; a substituted or unsubstituted $C_{6-60}$ arylamine; or a substituted or unsubstituted $C_{5-60}$ heteroaryl containing one or more hetero atoms selected from the group consisting of N, O, S and Si; or —Si($A_1$)($A_2$)($A_3$), $A_1$, $A_2$ and $A_3$ are each independently a substituted or unsubstituted $C_{1-60}$ alkyl; a substituted or unsubstituted $C_{3-10}$ cycloalkyl; a substituted or unsubstituted $C_{6-60}$ aryl; a substituted or unsubstituted $C_{5-60}$ heteroaryl containing one or more hetero atoms selected from the group consisting of N, O, S and Si; a monovalent non-aromatic condensed polycyclic group; or a monovalent non-aromatic hetero-condensed polycyclic group, $R_4$ and $R_5$ are each independently hydrogen; deuterium; halogen; or a substituted or unsubstituted $C_{1-60}$ alkyl, $R_6$ is hydrogen; or deuterium.

m and o are each independently an integer of 0 to 3, and n is an integer of 0 to 4.

According to another aspect of the present disclosure, there is provided an organic light emitting device comprising: a first electrode; a second electrode that is provided opposite to the first electrode; and one or more organic material layers that are provided between the first electrode and the second electrode, wherein at least one layer of the organic material layers includes the above-mentioned compound of the present disclosure.

Advantageous Effects

The compound represented by the Chemical Formula 1 can be used as a material of an organic material layer of an organic light emitting device. In particular, the compound can be used as a light emitting layer material of the organic light emitting device, can be subjected to a solution process, and further can improve the efficiency, achieve low driving voltage and/or improve lifetime characteristics in the organic light emitting device.

BRIEF DESCRIPTION OF THE DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, a light emitting layer 7, an electron transport layer 8 and a cathode 4.

FIGS. 3 to 5 show the results of LC-MS (Liquid Chromatography Mass Spectrometry) of Compounds 1 to 3 of Examples, respectively.

FIG. 6 shows the results of TGA (thermogravimetric analysis) of Compounds 1 to 3 of Examples.

DETAILED DESCRIPTION OF THE EMBODIMENTS

Hereinafter, embodiments of the present disclosure will be described in more detail to facilitate understanding of the invention.

(Compound)

A compound represented by the following Chemical Formula 1 is provided herein:

[Chemical Formula 1]

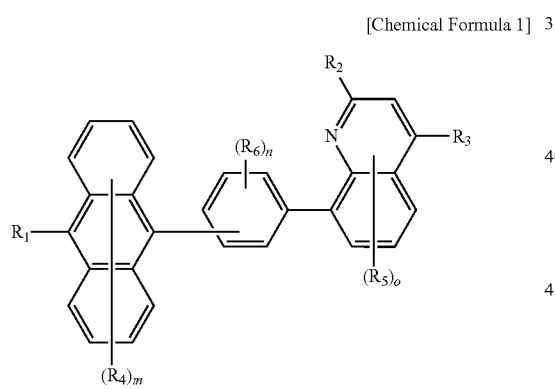

in the Chemical Formula 1, $R_1$ is a substituted or unsubstituted $C_{6-60}$ aryl.

$R_2$ and $R_3$ are each independently a substituted or unsubstituted $C_{3-10}$ cycloalkyl; a substituted or unsubstituted $C_{6-60}$ aryl; a substituted or unsubstituted $C_{6-60}$ arylamine; or a substituted or unsubstituted $C_{5-60}$ heteroaryl containing one or more hetero atoms selected from the group consisting of N, O, S and Si; or —Si($A_1$)($A_2$)($A_3$), $A_1$, $A_2$ and $A_3$ are each independently a substituted or unsubstituted $C_{1-60}$ alkyl; a substituted or unsubstituted $C_{3-10}$ cycloalkyl; a substituted or unsubstituted $C_{6-60}$ aryl; a substituted or unsubstituted $C_{5-60}$ heteroaryl containing one or more hetero atoms selected from the group consisting of N, O, S and Si; a monovalent non-aromatic condensed polycyclic group; or a monovalent non-aromatic hetero-condensed polycyclic group, $R_4$ and $R_5$ are each independently hydrogen; deuterium; halogen; or a substituted or unsubstituted $C_{1-60}$ alkyl, $R_6$ is hydrogen; or deuterium, m and o are each independently an integer of 0 to 3, and n is an integer of 0 to 4.

As used herein, the notation ⸺ or ⸺ means a bond linked to another substituent group.

As used herein, the term "substituted or unsubstituted" means being unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group containing at least one of N, O and S atoms, or being unsubstituted or substituted with a substituent to which two or more substituents of the above-exemplified substituents are connected. For example, "a substituent in which two or more substituents are connected" may be a biphenyl group. Namely, a biphenyl group may be an aryl group, or it may be interpreted as a substituent in which two phenyl groups are connected.

In the present disclosure, the carbon number of a carbonyl group is not particularly limited, but is preferably 1 to 40. Specifically, the carbonyl group may be a compound having the following structural formulas, but is not limited thereto.

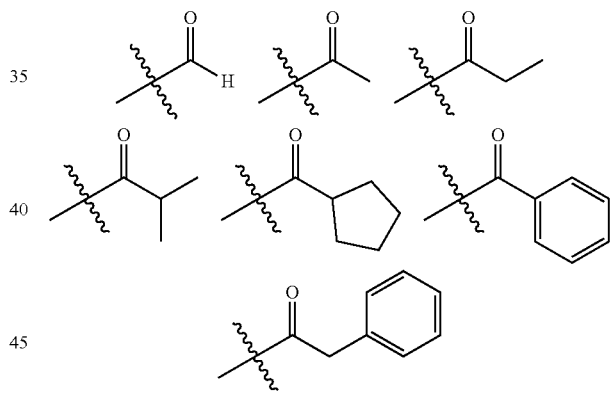

In the present disclosure, an ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be a compound having the following structural formulas, but is not limited thereto.

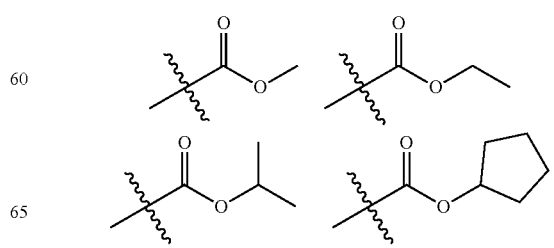

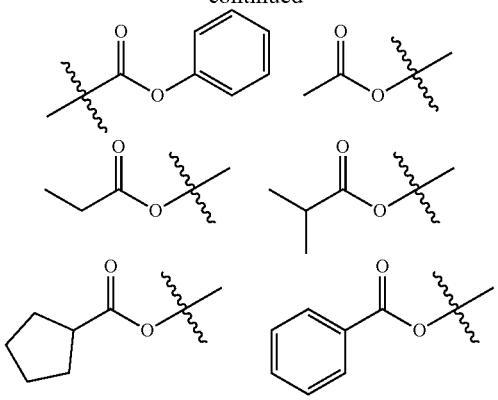

In the present disclosure, the carbon number of an imide group is not particularly limited, but is preferably 1 to 25. Specifically, the imide group may be a compound having the following structural formulas, but is not limited thereto.

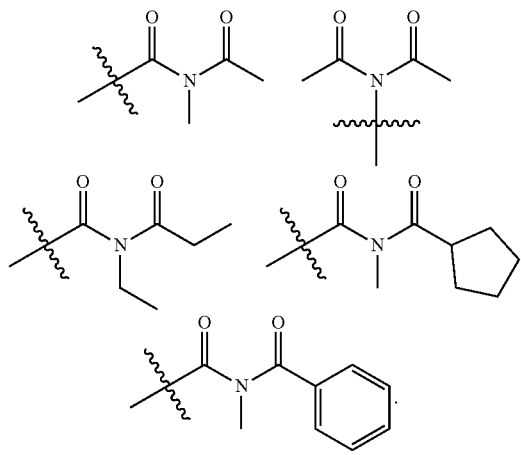

In the present disclosure, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present disclosure, a boron group specifically includes a trimethylboron group, a triethylboron group, a t-butyldimethylboron group, a triphenylboron group, and a phenylboron group, but is not limited thereto.

In the present disclosure, examples of a halogen group include fluorine, chlorine, bromine, or iodine.

In the present disclosure, the alkyl group may be straight-chain or branched-chain, and the carbon number thereof is not particularly limited, but is preferably 1 to 40. According to one embodiment, the carbon number of the alkyl group is 1 to 20. According to another embodiment, the carbon number of the alkyl group is 1 to 10. According to another embodiment, the carbon number of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethylpropyl, isohexyl, 2-methylpentyl, 4-methylhexyl, 5-methylhexyl, and the like, but are not limited thereto.

In the present disclosure, the alkenyl group may be straight-chain or branched-chain, and the carbon number thereof is not particularly limited, but is preferably 2 to 40. According to one embodiment, the carbon number of the alkenyl group is 2 to 20. According to another embodiment, the carbon number of the alkenyl group is 2 to 10. According to still another embodiment, the carbon number of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, a cycloalkyl group is not particularly limited, but the carbon number thereof is preferably 3 to 60. According to one embodiment, the carbon number of the cycloalkyl group is 3 to 30. According to another embodiment, the carbon number of the cycloalkyl group is 3 to 20. According to still another embodiment, the carbon number of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present disclosure, an aryl group is not particularly limited, but the carbon number thereof is preferably 6 to 60, and it may be a monocyclic aryl group or a polycyclic aryl group. According to one embodiment, the carbon number of the aryl group is 6 to 30. According to one embodiment, the carbon number of the aryl group is 6 to 20. The aryl group may be a phenyl group, a biphenyl group, a terphenyl group or the like as the monocyclic aryl group, but is not limited thereto. The polycyclic aryl group includes a naphthyl group, an anthracenyl group, a phenanthryl group, a pyrenyl group, a perylenyl group, a chrysenyl group, or the like, but is not limited thereto.

In the present disclosure, a heterocyclic group is a heterocyclic group containing one or more of O, N, Si and S as a heteroatom, and the carbon number thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazol group, a benzocarbazole group, a benzothiophene group, a dibenzothiophene group, a benzofuranyl group, a phenanthroline group, a triazoly group, an isoxazolyl group, an oxadiazoly group, a thiadiazolyl group, a benzothiazolyl group, a phenothiazinyl group, a dibenzofuranyl group, and the like, but are not limited thereto.

In the present disclosure, the aryl group in the aralkyl group, the aralkenyl group, the alkylaryl group and the arylamine group is the same as the aforementioned examples of the aryl group. In the present disclosure, the alkyl group in the aralkyl group, the alkylaryl group and the alkylamine group is the same as the aforementioned examples of the alkyl group. In the present disclosure, the heteroaryl in the heteroarylamine can be applied to the aforementioned description of the heterocyclic group. In the present disclosure, the alkenyl group in the aralkenyl group is the same as the aforementioned examples of the alkenyl group. In the present disclosure, the aforementioned description of the aryl group may be applied except that the arylene is a divalent group. In the present disclosure, the aforementioned description of the heterocyclic group can be applied except that the heteroarylene is a divalent group. In the present disclosure, the aforementioned description of the aryl group or cycloalkyl group can be applied except that the hydrocarbon ring is not a monovalent group but formed by combining two substituent groups. In the present disclosure, the aforementioned description of the heterocyclic group can be applied, except that the heterocyclic group is not a monovalent group but formed by combining two substituent groups.

In the present disclosure, the monovalent non-aromatic condensed polycyclic group means a monovalent group in which two or more rings are condensed with each other, the group contains only carbon as a ring-forming atom, and the whole molecule has a non-aromaticity. Specific examples of the monovalent non-aromatic condensed polycyclic group include a fluorenyl group and the like. In the present disclosure, a divalent non-aromatic condensed polycyclic group means a divalent group having the same structure as the above-mentioned monovalent non-aromatic condensed polycyclic group.

In the present disclosure, the fluorenyl group may be substituted, and two substituents may be linked with each other to form a spiro structure. In the case where the fluorenyl group is substituted.

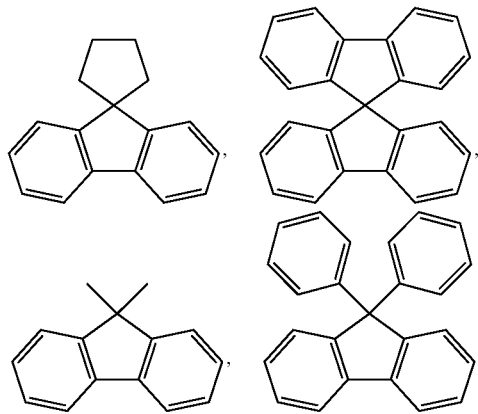

and the like can be formed. However, the structure is not limited thereto.

In the present disclosure, the monovalent non-aromatic hetero-condensed polycyclic group means a monovalent group in which two or more rings are condensed with each other, the group contains a hetero atom selected from N, O, Si, P, and S in addition to carbon as a ring-forming atom, and the entire molecule has non-aromaticity. In the present disclosure, a divalent non-aromatic condensed polycyclic group means a divalent group having the same structure as the above-mentioned monovalent non-aromatic hetero-condensed polycyclic group.

Preferably, the compound represented by Chemical Formula 1 may be a compound represented by the following Chemical Formula 2 or Chemical Formula 3:

[Chemical Formula 2]

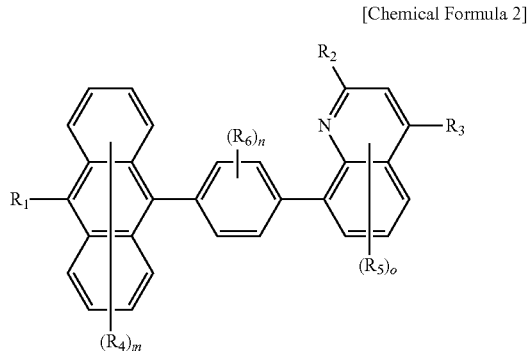

[Chemical Formula 3]

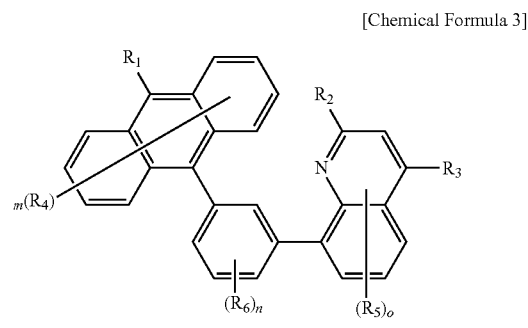

wherein, $R_1$, $R_2$, $R_3$, $R_4$, $R_5$, $R_6$, m, n and o are as defined above.

Preferably, $R_1$ may be phenyl; biphenylyl; terphenylyl; quarterphenylyl; naphthyl; phenanthrenyl; triphenylenyl; chrysenyl; fluoranthenyl; pyrenyl; or triphenylenyl. More preferably, $R_1$ may be phenyl; or naphthyl.

Preferably, $R_2$ and $R_3$ may each independently be any one selected from the group consisting of:

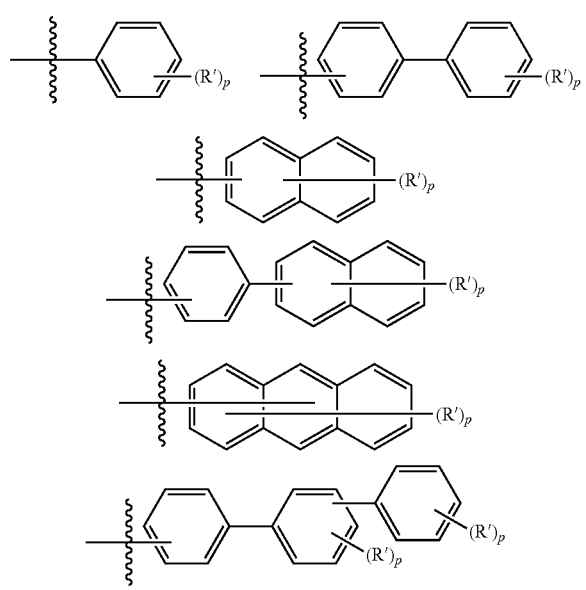

-continued
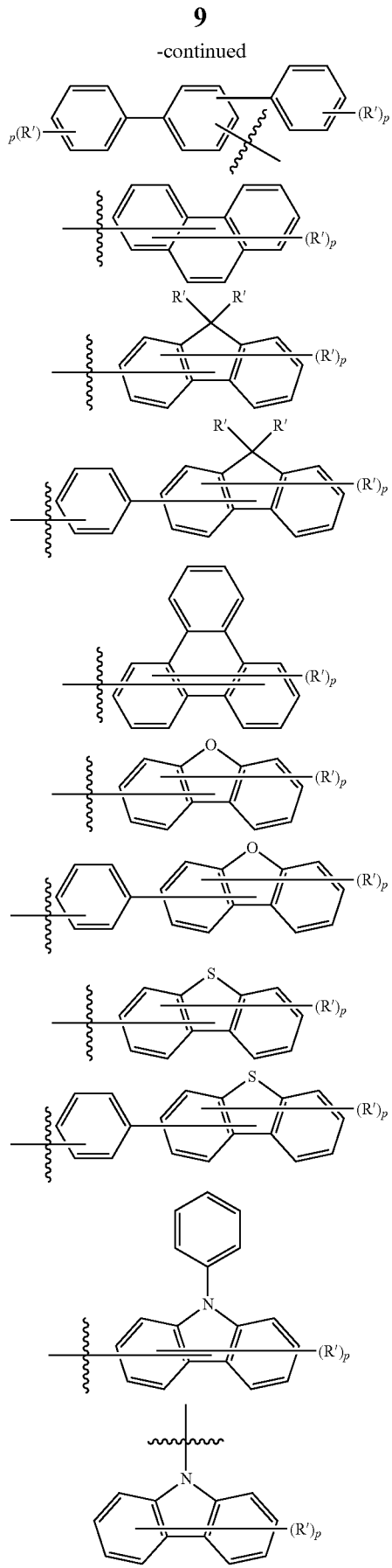
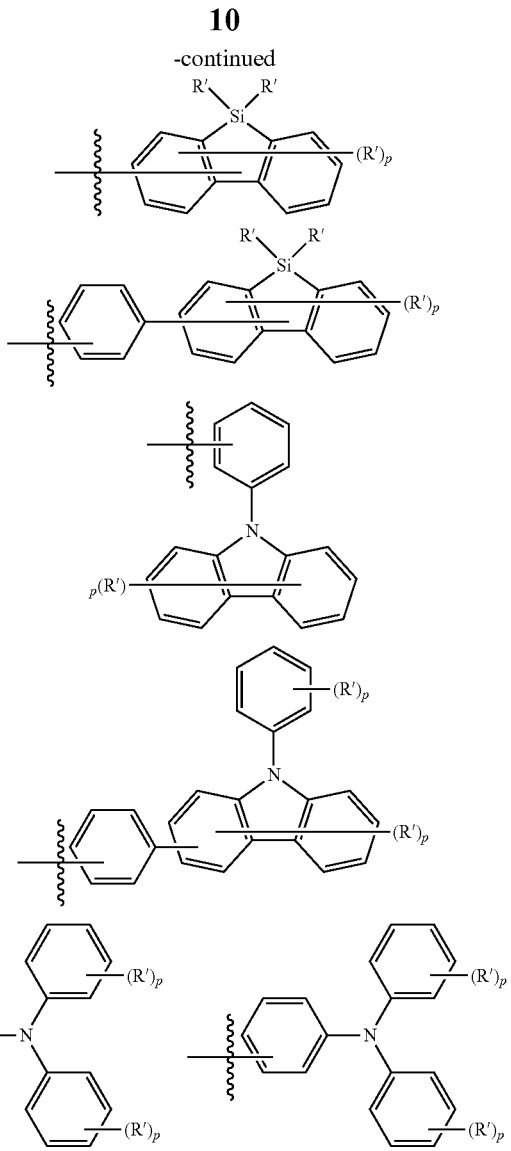
wherein,
R' are each independently hydrogen; deuterium; halogen; or a substituted or unsubstituted $C_{1-60}$ alkyl, and
each p is independently an integer of 0 to 3.
Preferably, R' is hydrogen; or $C_{1-10}$ alkyl.
Preferably, the compound represented by Chemical Formula 1 may be any one selected from the group consisting of:
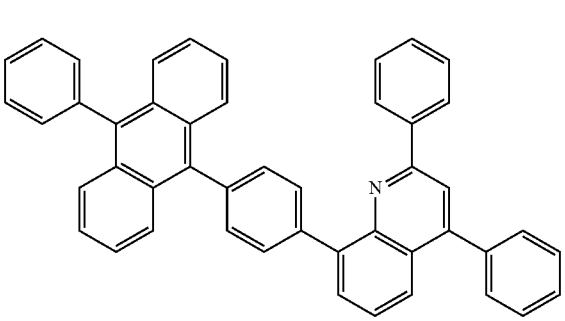

-continued
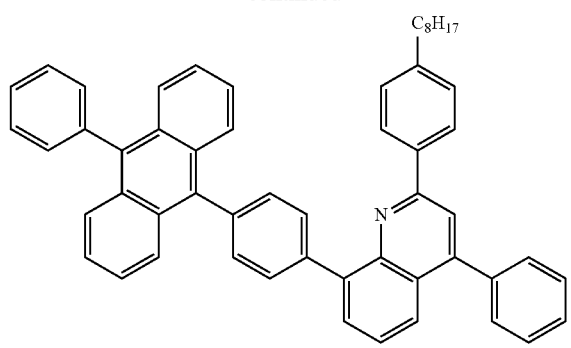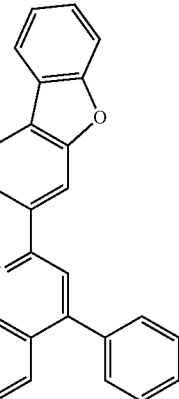
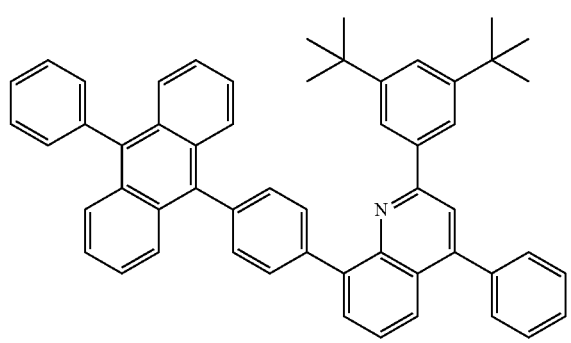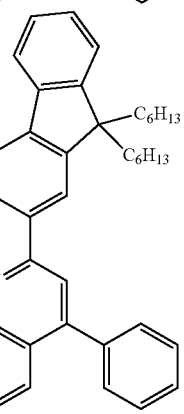
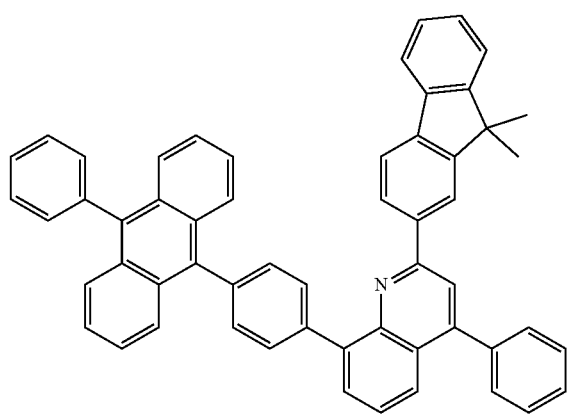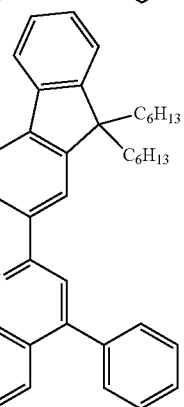
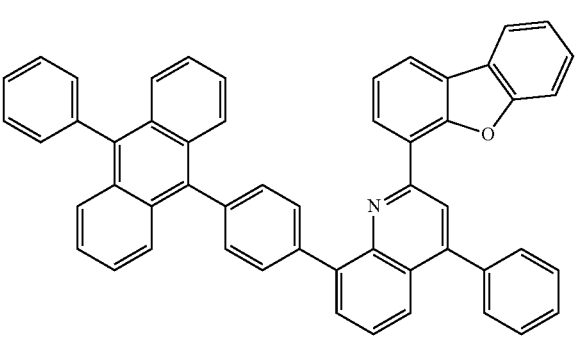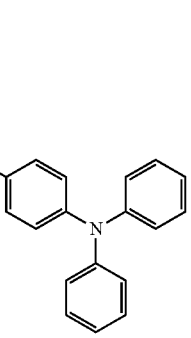
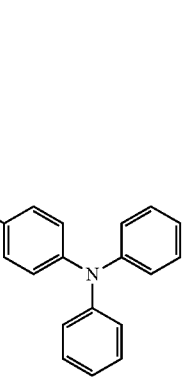

-continued
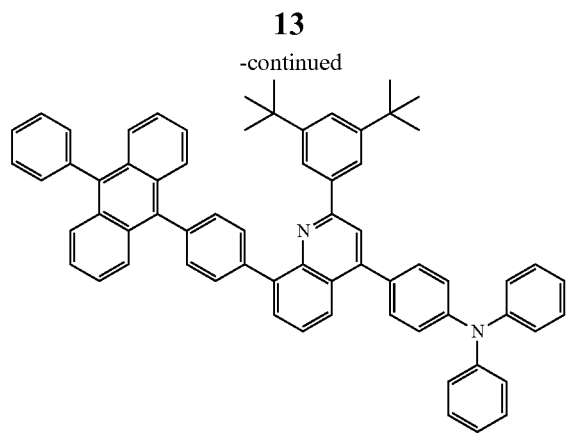
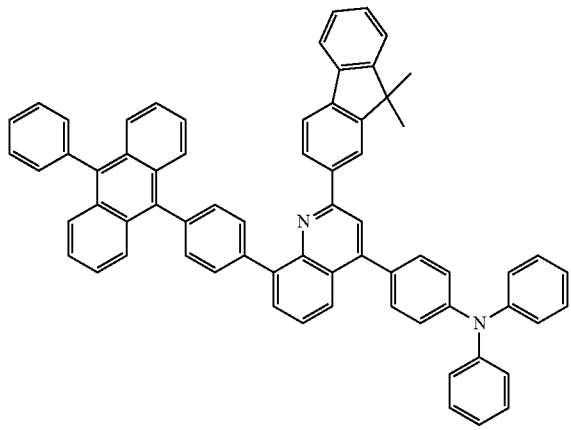
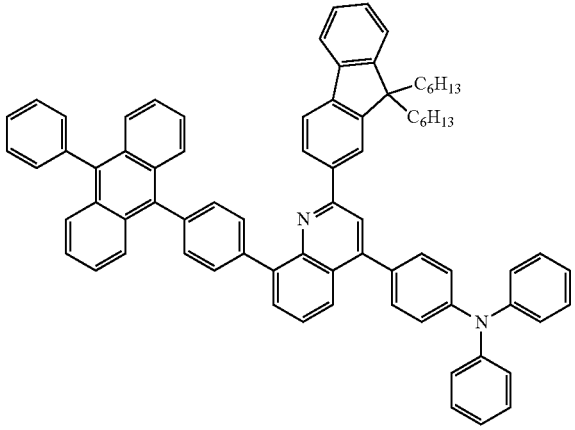
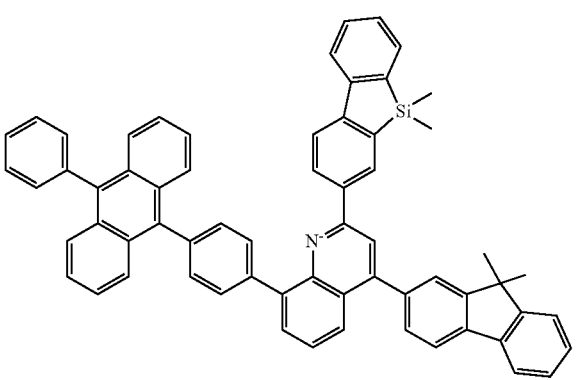
-continued
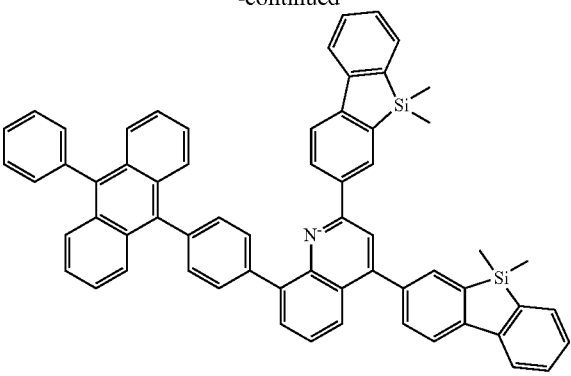
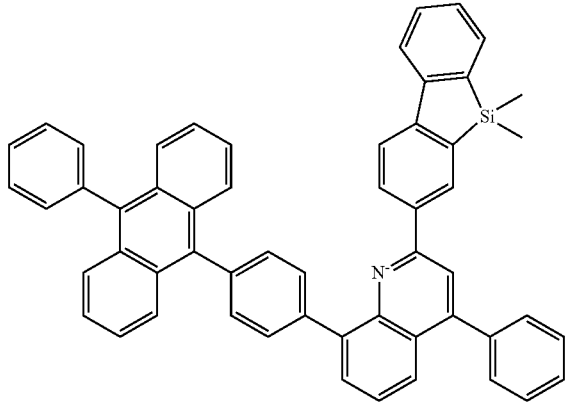
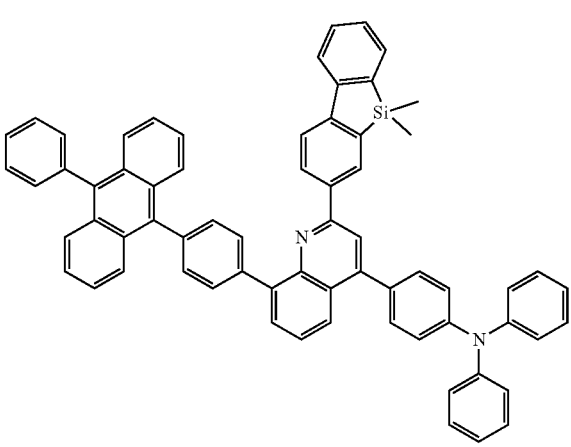
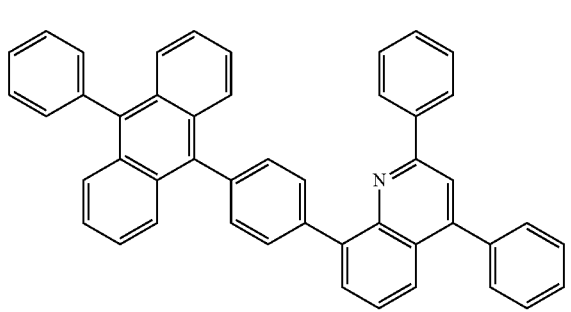

-continued
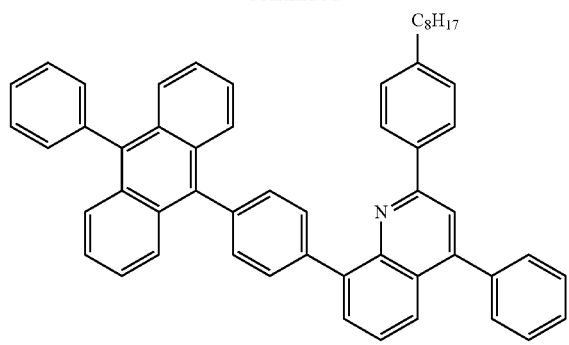
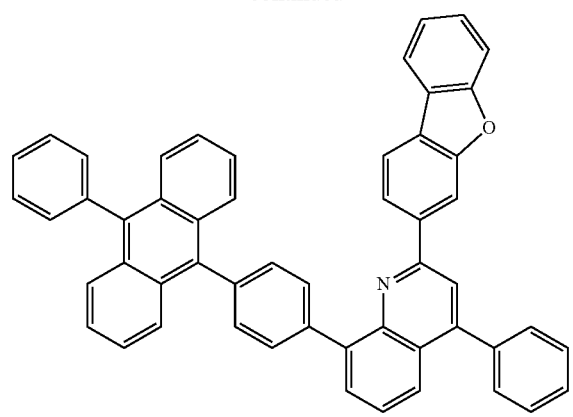
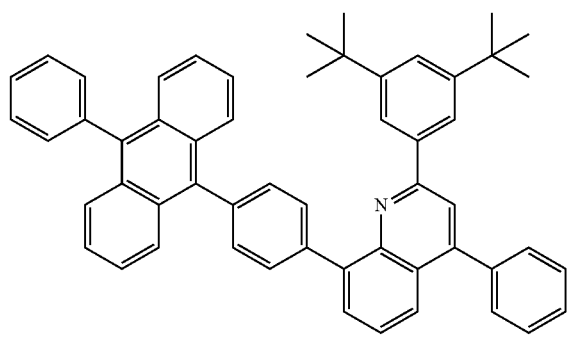
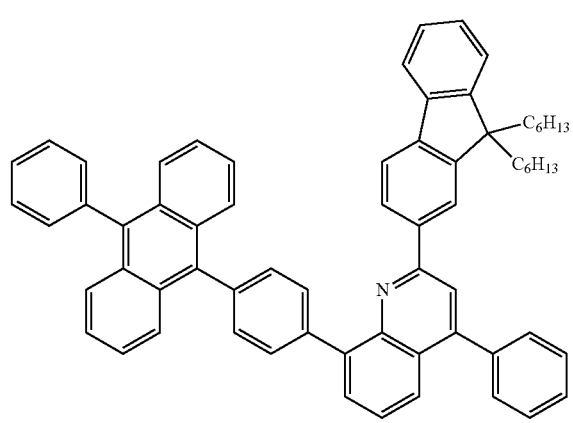
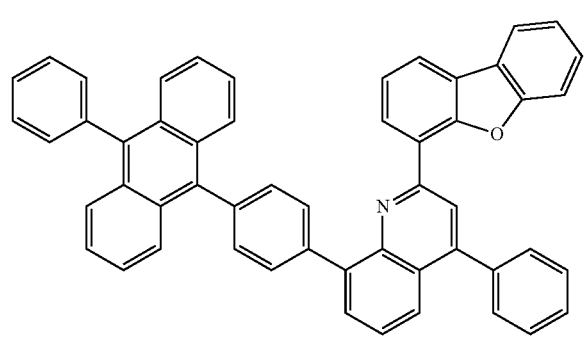
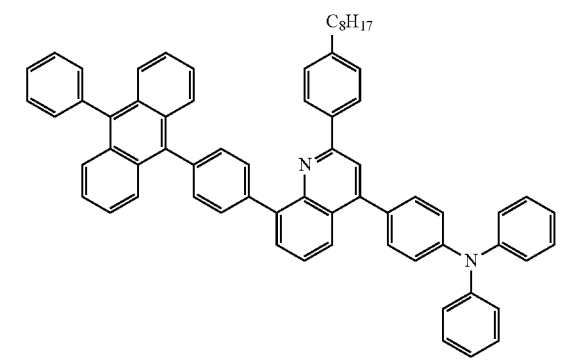

17
-continued
18
-continued
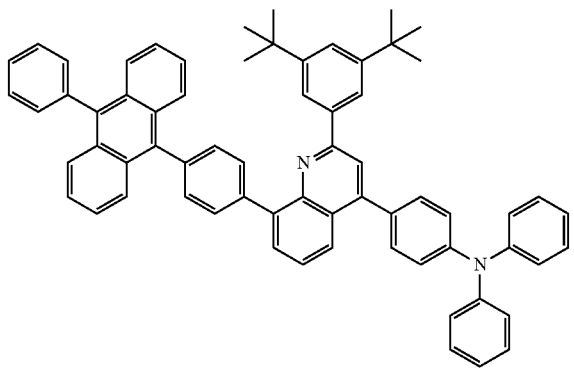
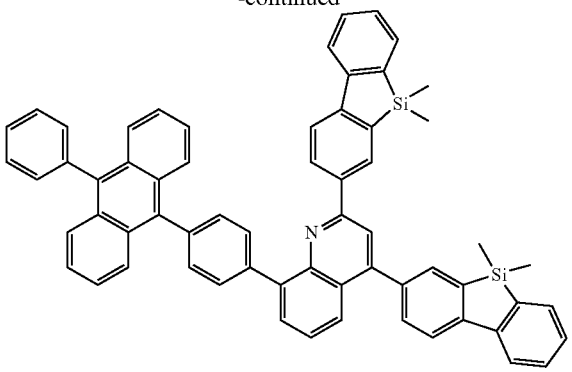
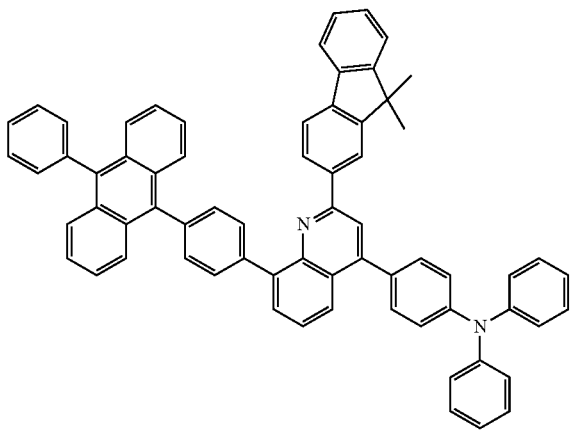
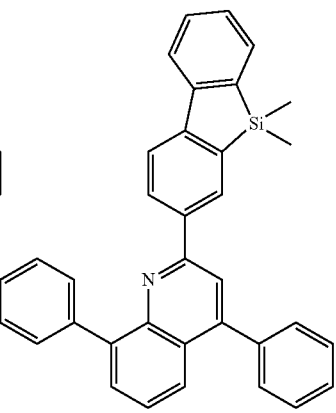
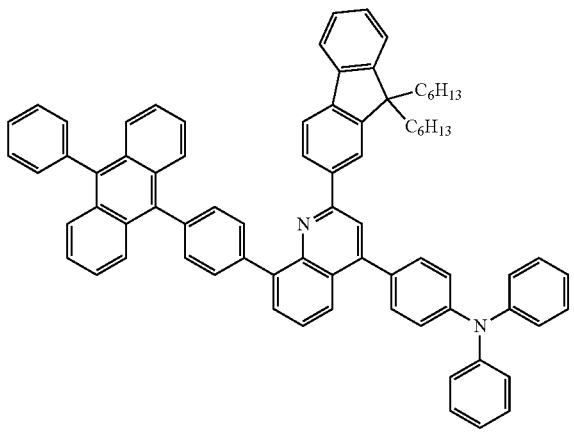
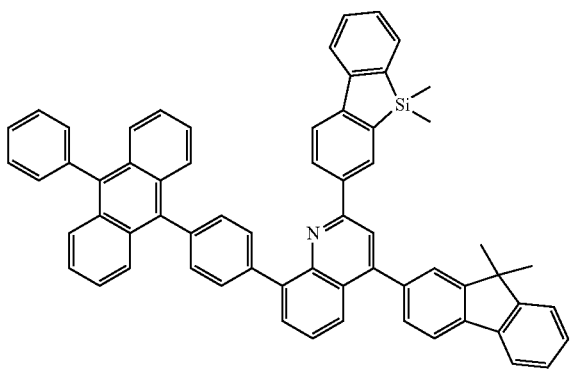

-continued
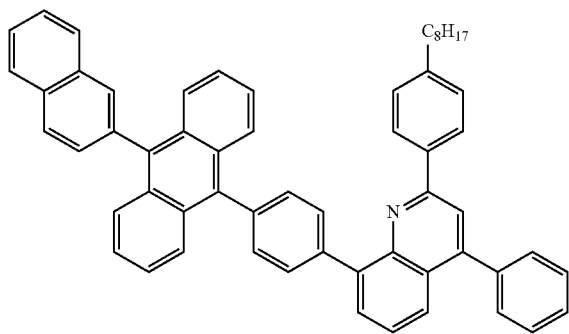
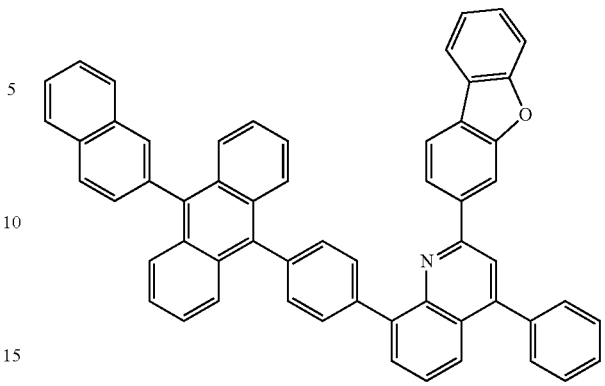
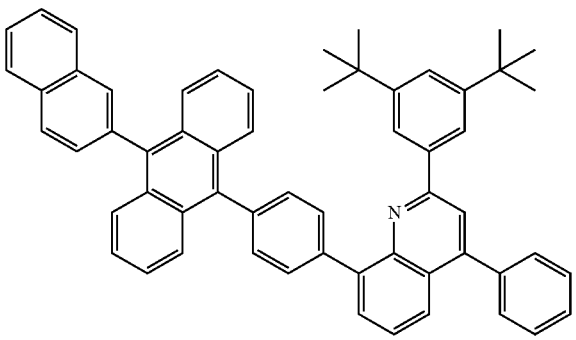
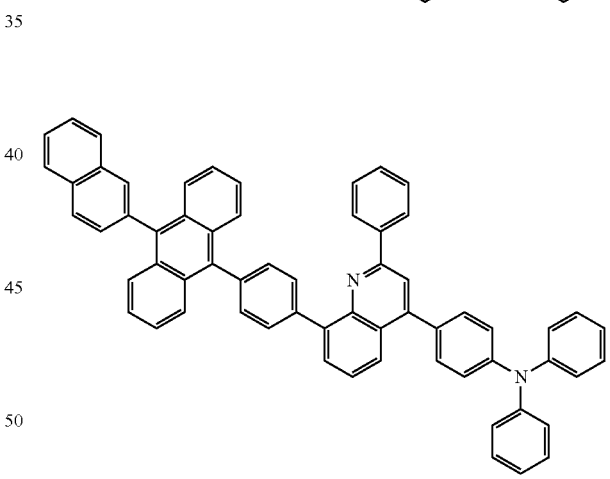
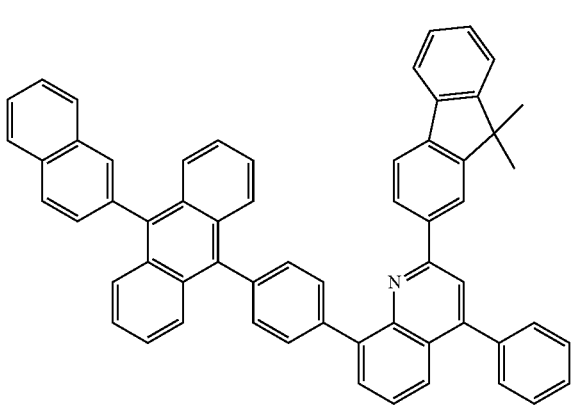
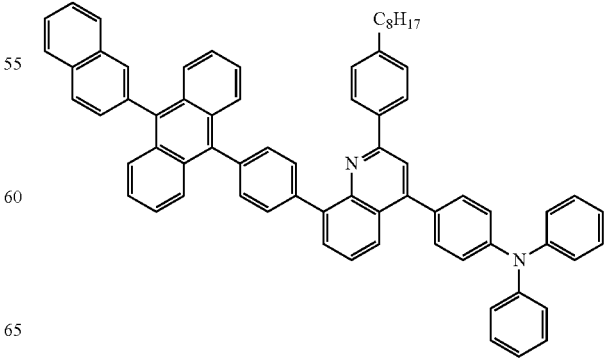

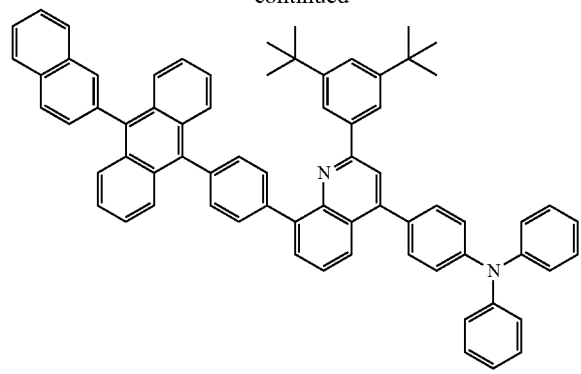
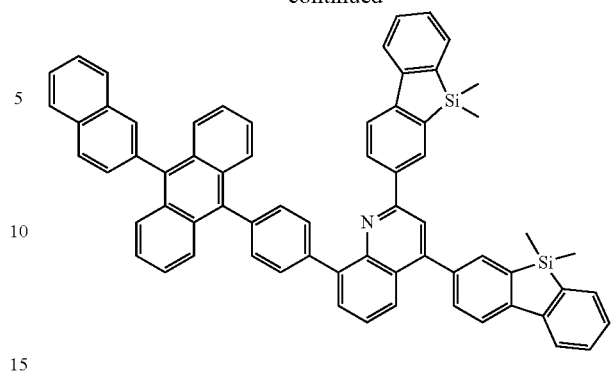
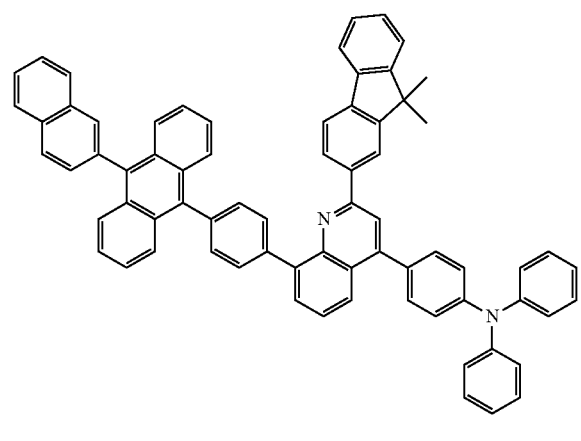
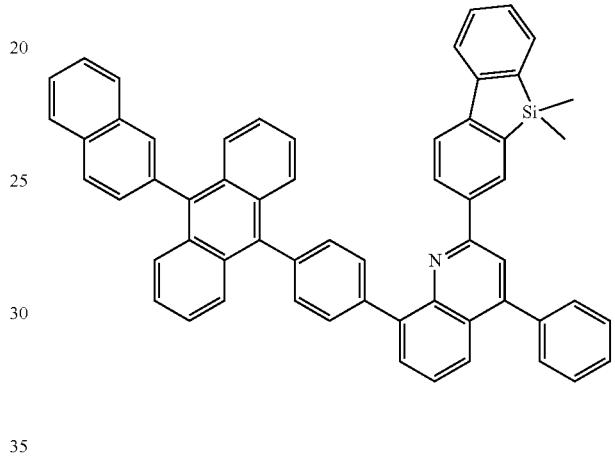
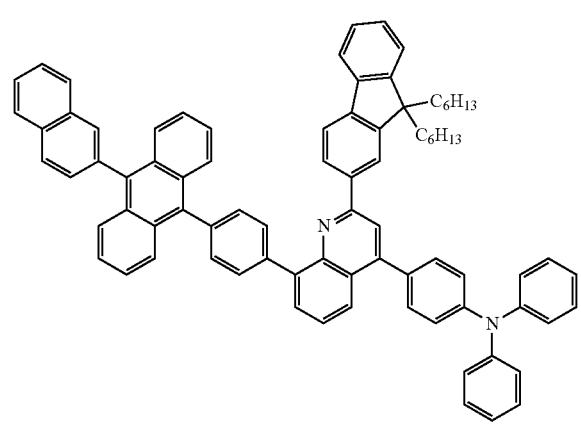
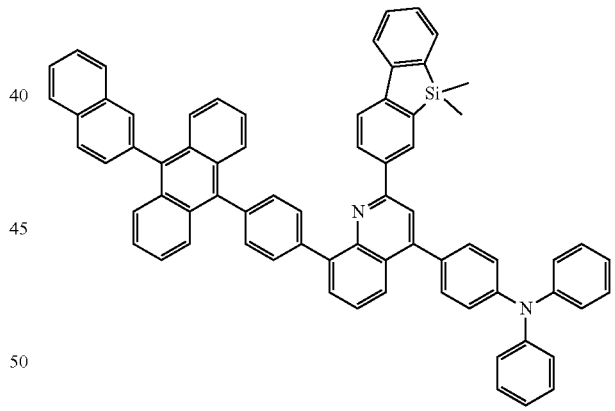
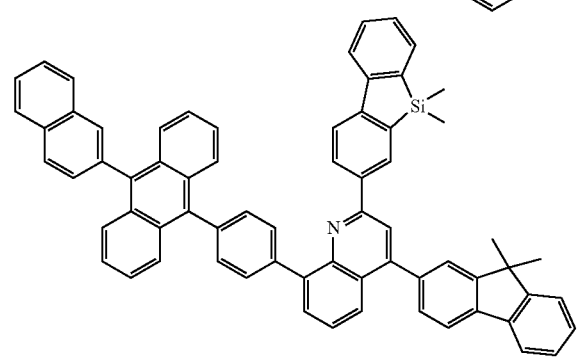
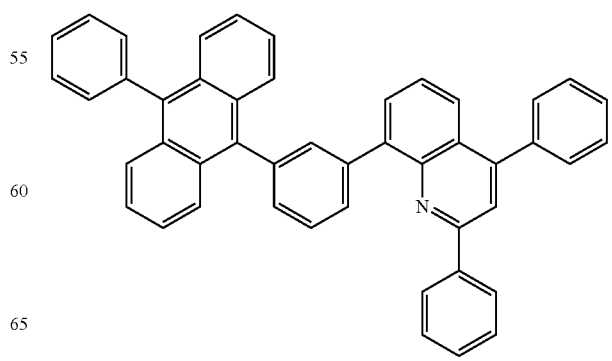

-continued

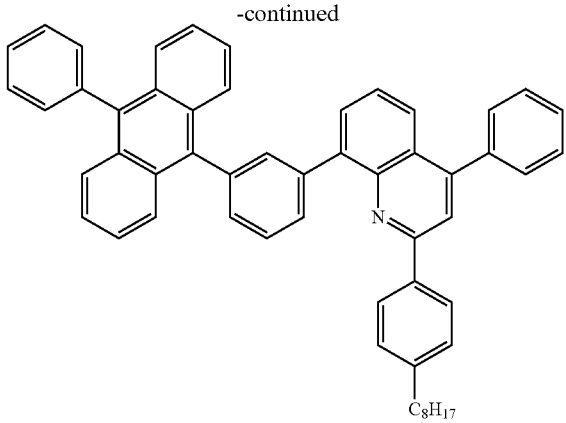

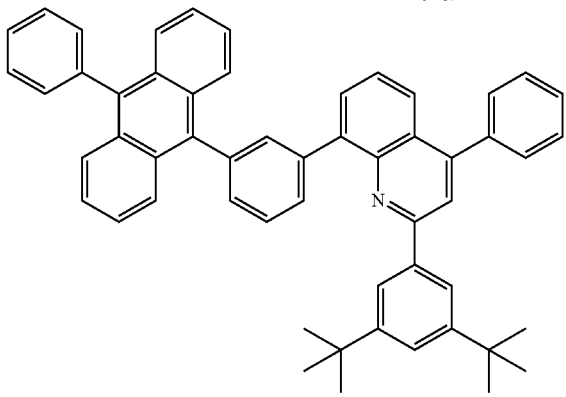

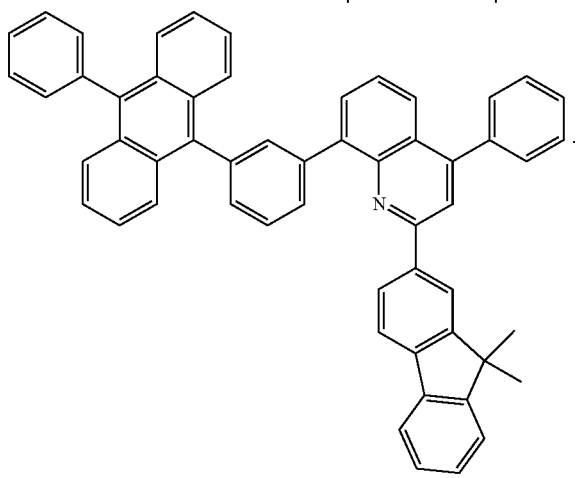

The compound represented by Chemical Formula 1 according to the present disclosure includes a quinoline substituent linked to an anthracene by a phenylene linker. Thereby, when applied to the light emitting layer of the organic light emitting device, since the compound can improve the electron transfer characteristics, it can significantly improve the light emitting efficiency in the light emitting device having a high hole transfer rate, and can allow the solution process to be performed.

In particular, due to the influence of the quinoline structure which is an electrophilic group, it is possible to form a host of an n-type or bipolar type organic light emitting layer (EML) compared to an aromatic carbon type monomolecular material, whereby the charge balance in the EML can be effectively adjusted. Further, it is possible to easily substitute additional substituents ($R_2$, $R_3$) in the quinoline, making it possible to perform the solution process.

In particular, since anthracene is linked via a phenylene linker at the 8th position of quinoline, it can deepen the distortion of anthracene than when linked by a naphthalene linker or another polycyclic aryl linker, thereby realizing a molecular form suitable for blue host. N of quinoline is suitable for inducing a structural stability by a secondary bond with adjacent quinoline substituent $R_2$ and thus realizing effects such as high thermal stability. Moreover, the compound can be synthesized so that $R_2$ and $R_3$ are positioned at intervals where one carbon atom is placed between them, it can enhance orbital distribution and enhancing rotational freedom independent of each other relative to the isoquinoline structure, and thus can derive the physical properties suitable for a solution process, such as increasing solubility. In addition, the central 9th position of anthracene is linked to quinoline by a phenylene linker, thereby making it possible to realize an effect of increasing the stability of anthracene and improve the lifetime.

The compound represented by Chemical Formula 1 may be prepared by a method based on the multi-step reaction of Reaction Schemes 1-1 to 1-2 below. The preparation method may be more specifically described in the Preparation Examples described below.

[Reaction Scheme 1-1]

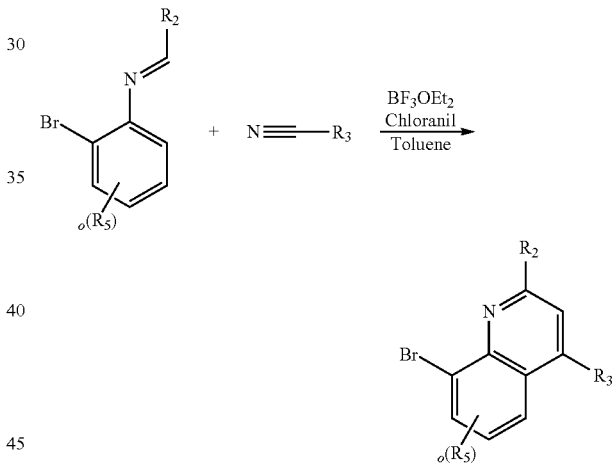

[Reaction Scheme 1-2]

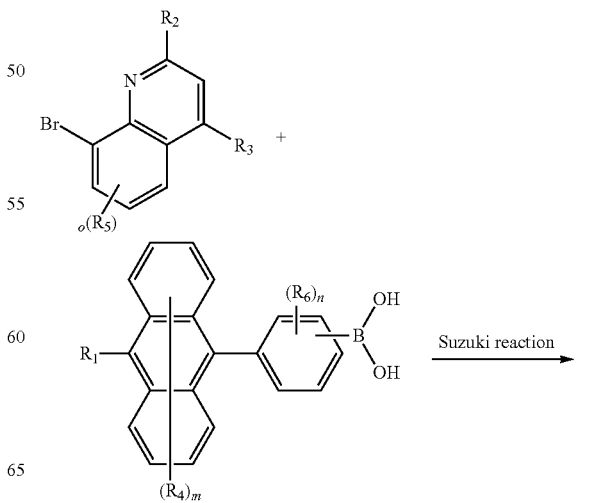

-continued

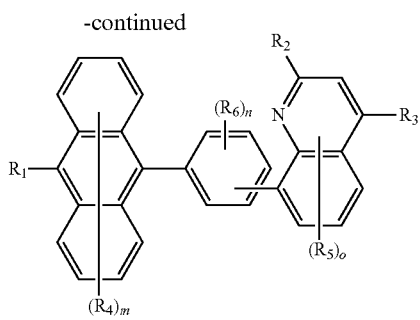

in the Reaction Schemes 1-1 and 1-2, $R_1$, $R_2$, $R_3$, $R_4$, $R_5$, $R_6$, m, n and o are as defined above. In the above Reaction Schemes 1-1 and 1-2, the reactive group, catalyst, solvent, and the like used can be changed to comply with the desired product.

(Coating Composition)

The compound according to the present disclosure can form an organic material layer, particularly a light emitting layer, of an organic light emitting device by a solution process. Thus, the present disclosure provides a coating composition comprising the above-mentioned compound according to the present disclosure and a solvent.

The solvent is not particularly limited as long as it is a solvent capable of dissolving or dispersing the compound according to the present disclosure. Examples of the solvent may include chlorine-based solvents such as chloroform, methylene chloride, 1,2-dichloroethane, 1,1,2-trichloroethane, chlorobenzene and o-dichlorobenzene; ether-based solvents such as tetrahydrofuran and dioxane; aromatic hydrocarbon-based solvents such as toluene, xylene, trimethylbenzene and mesitylene; aliphatic hydrocarbon-based solvents such as cyclohexane, methylcyclohexane, n-pentane, n-hexane, n-heptane, n-octane, n-nonane and n-decane; ketone-based solvents such as acetone, methyl ethyl ketone, and cyclohexanone; ester-based solvents such as ethyl acetate, butyl acetate and ethyl cellosolve acetate; polyalcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin and 1,2-hexanediol, and derivatives thereof; alcohol-based solvents such as methanol, ethanol, propanol, isopropanol and cyclohexanol; sulfoxide-based solvents such as dimethyl sulfoxide; amide-based solvents such as N-methyl-2-pyrrolidone and N,N-dimethylformamide; benzoate-based solvents such as butyl benzoate and methyl-2-methoxybenzoate; tetraline; 3-phenoxy-toluene, and the like. In addition, the above-mentioned solvents may be used singly or in combination of two or more solvents.

Further, the viscosity of the coating composition is preferably 1 cP to 10 cP, and coating is easy within the above range. Further, in the coating composition, the concentration of the compound according to the present disclosure is preferably 0.1 wt/v % to 20 wt/v %.

In addition, the coating composition may further include one or more additives selected from the group consisting of an antioxidant and a photo-stabilizer.

In another embodiment of the present disclosure, there is provided a method for forming a light emitting layer using the above-mentioned coating composition. Specifically, the method includes the steps of: coating the above-mentioned coating composition according to the present disclosure on the anode or on the light emitting layer formed on the anode by a solution process; and heat treating the coated coating composition.

The solution process uses the coating composition according to the present disclosure, and refers to spin coating, dip coating, doctor blading, inkjet printing, screen printing, spray method, roll coating, and the like, but is not limited thereto.

The heat treatment temperature in the heat treatment is preferably from 150 to 230° C. In another embodiment, a heat treatment time may be from 1 minute to 3 hours, more preferably 10 minutes to 1 hour. In another embodiment, the heat treatment is preferably carried out in an inert gas atmosphere such as argon and nitrogen.

(Organic Light Emitting Device)

According to another aspect of the present disclosure, there is provided an organic light emitting device. Specifically, the present disclosure provides an organic light emitting device comprising: an anode; a cathode that is provided opposite to the anode; a light emitting layer that is provided between the anode and the cathode; and a hole transport layer that is provided between the anode and the light emitting layer, wherein the light emitting layer includes the compound according to the present disclosure.

The structure of an organic light emitting device according to an embodiment of the present disclosure is illustrated in FIGS. 1 and 2.

FIG. 1 shows an example of an organic light emitting device comprising a substrate 1, an anode 2, a light emitting layer 3, and a cathode 4. FIG. 2 shows an example of an organic light emitting device comprising a substrate 1, an anode 2, a hole injection layer 5, a hole transport layer 6, a light emitting layer 7, an electron transport and injection layer 8, and a cathode 4.

The organic light emitting device according to the present disclosure may be manufactured by materials and methods known in the art, except that the light emitting layer includes the compound according to the present disclosure and is manufactured according to the above-described method.

For example, the organic light emitting device according to the present disclosure can be manufactured by sequentially stacking an anode, an organic material layer and a cathode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon.

In addition to such a method, the organic light emitting device may be manufactured by sequentially depositing a cathode material, an organic material layer and an anode material on a substrate (International Publication WO2003/012890). However, the manufacturing method is not limited thereto.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or SnO$_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to a hole injection layer or the electron injection material, and further is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene)(PPV)-based polymer; a spiro compound; polyfluorene, lubrene, and the like, but are not limited thereto.

As the light emitting layer, a compound of the present disclosure is used, and it can be used as a host material. The light emitting layer may further include a host material and a dopant material. The host material may be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto. Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which may receive electrons well from a cathode and transfer the electrons to a light emitting layer, and has a large mobility for electrons. Specific examples of the electron transport material include: an Al complex of 8-hydroxyquinoline; a complex including $Alq_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris (2-methyl-8-hydroxyquinolinato)aluminum, tris(8-hydroxyquinolinato)gallium, bis(10-hydroxybenzo[h]quinolinato) beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present disclosure may be a front side emission type, a back side emission type, or a double side emission type according to the used material.

In addition, the compound according to the present disclosure may be included in an organic solar cell or an organic transistor in addition to an organic light emitting device.

The preparation of the compound represented by Chemical Formula 1 according to the present disclosure and the organic light emitting device containing the same will be described in detail in the following examples. However, these examples are presented for illustrative purposes only, and are not intended to limit the scope of the present disclosure.

The preparation of the compound represented by Chemical Formula 1 and the organic light emitting device containing the same will be described in detail in the following examples. However, these examples are presented for illustrative purposes only, and are not intended to limit the scope of the present disclosure.

EXAMPLE

Example 1: Preparation of Compound 1

[Reaction Scheme 1-A]

(1) Synthesis of Intermediate Compound 1-A

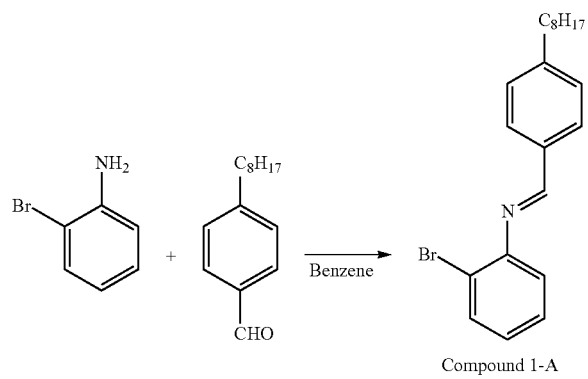

Compound 1-A

2-Bromoaniline (10 mmol), 4-octylbenzaldehyde (11 mmol) and benzene (50 mL) were mixed and refluxed for 12 hours or more. A small amount of the reaction intermediate was obtained, and the progress of reaction to Intermediate Compound 1-A was confirmed by TLC. When the reaction was confirmed, the next reaction was immediately performed without extraction or further purification.

[Reaction Scheme 1-B]

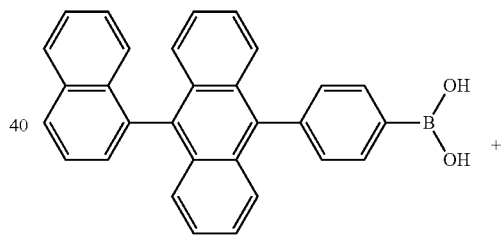

Compound 1-A

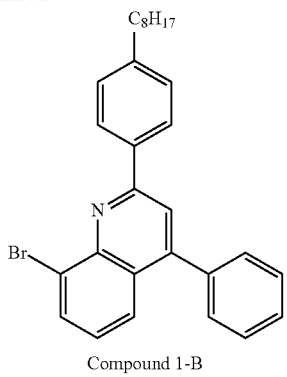

Compound 1-B

Toluene was injected into Intermediate Compound 1-A. Phenylacetylene (12 mmol), chloranil (15 mmol), and boron trifluoride diethyl etherate (12 mmol) were added thereto, and then refluxed for 24 hours. After completion of the reaction, the reaction mixture was extracted with MC, and column-purified under the conditions of hexane:MC=7:3, which was precipitated in methanol to give Intermediate Compound 1-B as a white powder (yield: 90%).

[Reaction Scheme 1]

(2) Synthesis of Compound 1

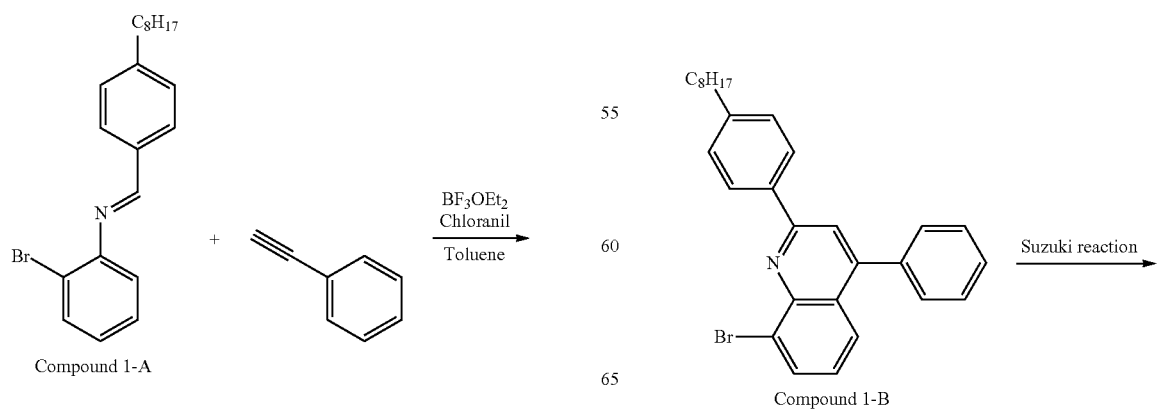

Compound 1-B

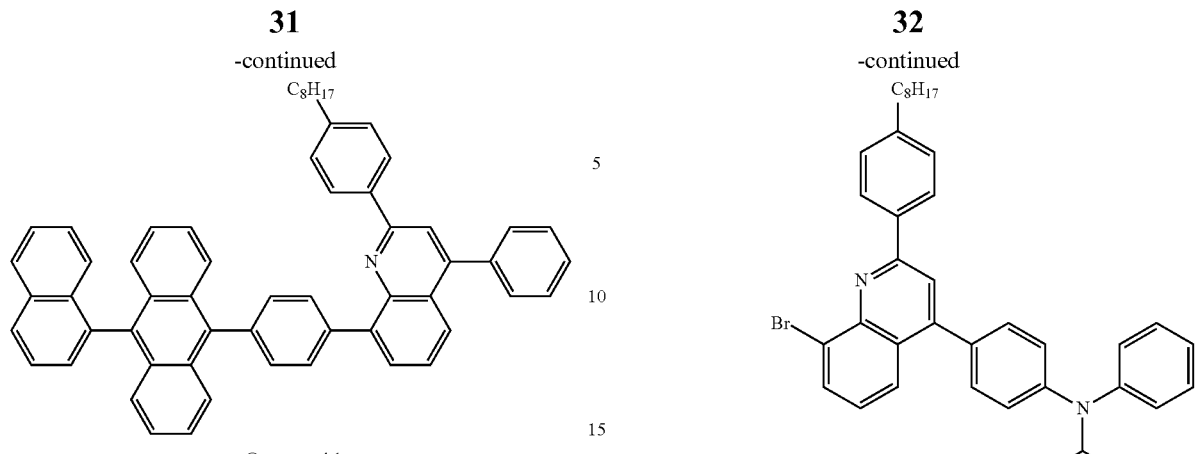

Compound 1

4-(10-(Naphthalen-1-yl)anthracen-9-yl)phenyl boric acid (4.5 mmol), Intermediate Compound 1-B (3 mmol) and Pd(pph₃)₄ (0.15 mmol) were dissolved in toluene (100 mL). K₂CO₃ aqueous solution (30 mmol/20 ml water) was added thereto and refluxed. After completion of the reaction, the reaction mixture was extracted with MC, and column-purified under the conditions of gradient hexane:MC=7:3, which was precipitated in methanol to give Compound 1 as a white powder (yield: 85%). The LCMS results of Compound 1 is shown in FIG. 3, and the TGA measurement graph is shown in FIG. 6.

Example 2: Synthesis of Compound 2

[Reaction Scheme 2-A]

(1) Synthesis of Intermediate Compound 2-A

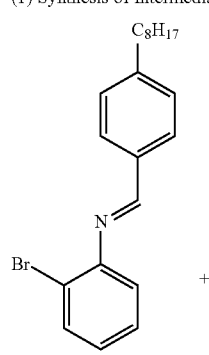

Compound 1-A

+

Compound 2-A

4-Ethynyltriphenylamine (12 mmol), chloranil (15 mmol) and boron trifluoride diethyl etherate (12 mmol) were added to Intermediate Compound 1-A of Example 1 and refluxed for 24 hours. After completion of the reaction, the reaction mixture was extracted with MC, and column-purified under the conditions of gradient hexane:MC=7:3, which was precipitated in methanol to give Intermediate Compound 2-A as a white powder (yield: 90%).

[Reaction Scheme 2]

(2) Synthesis of Intermediate Compound 2

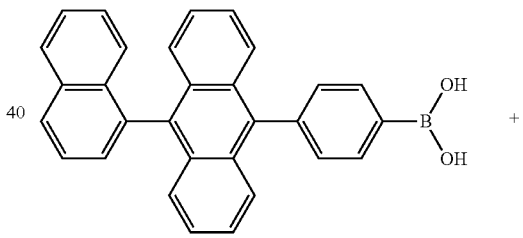

+

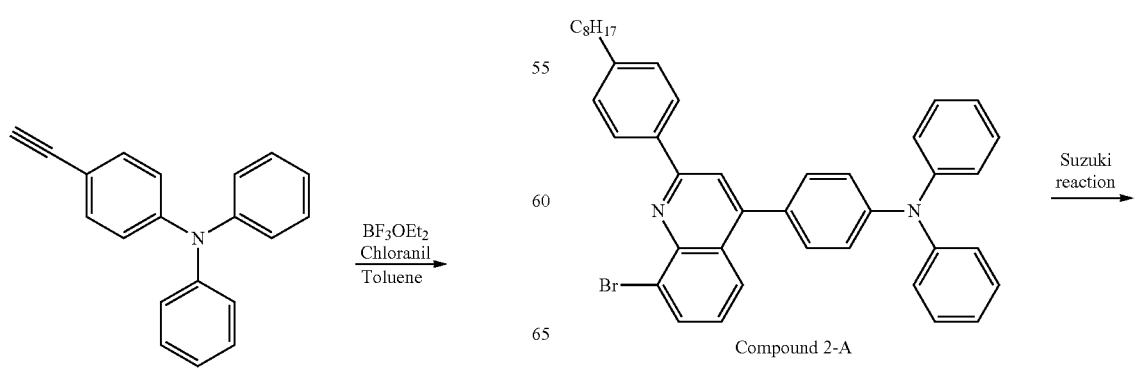

Compound 2-A

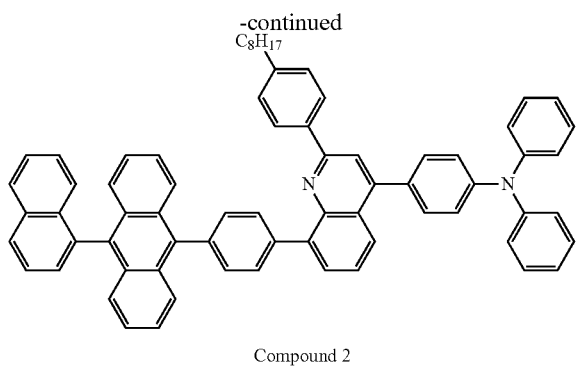

Compound 2

4-(10-(Naphthalen-1-yl)anthracen-9-yl)phenyl boric acid (4.5 mmol), Intermediate Compound 2-A (3 mmol) and Pd (pph$_3$)$_4$ (0.15 mmol) were dissolved in toluene (100 mL). K$_2$CO$_3$ aqueous solution (30 mmol/20 ml water) was added thereto and refluxed. After completion of the reaction, the reaction mixture was extracted with MC, and column-purified under the conditions of gradient hexane:MC=7:3, which was precipitated in methanol to give Compound 2 as a white powder (yield: 75%). The LCMS results of Compound 2 is shown in FIG. 4, and the TGA measurement graph is shown in FIG. 6.

Example 3: Synthesis of Compound 3

[Reaction Scheme 3-A]

(1) Synthesis of Intermediate Compound 3-A

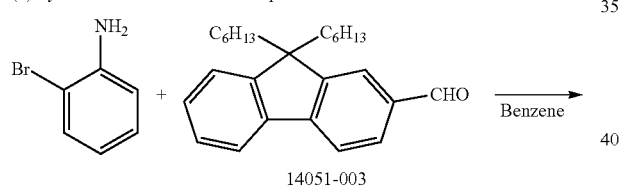

14051-003

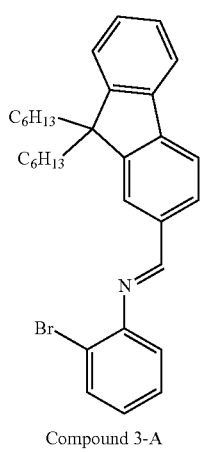

Compound 3-A

2-Bromoaniline (10 mmol), 14051-003 (11 mmol) and benzene (50 mL) were mixed and refluxed for 12 hours or more. A small amount of the reaction intermediate was obtained, and the progress of reaction to Intermediate Compound 3-A was confirmed by TLC. When the reaction was confirmed, the next reaction was immediately performed without extraction or further purification.

[Reaction Scheme 3-B]

(2) Synthesis of Intermediate Compound 3-B

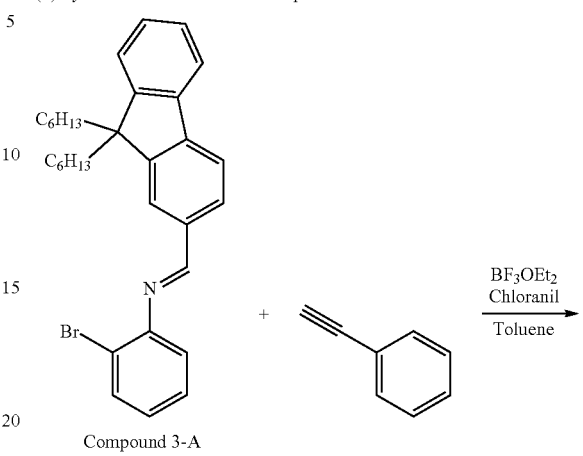

Compound 3-A

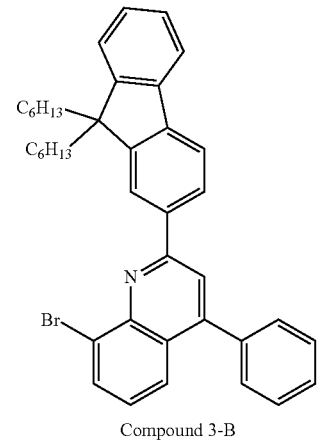

Compound 3-B

Toluene was injected into Intermediate Compound 3-A. Phenylacetylene (12 mmol), chloranil (15 mmol), and boron trifluoride diethyl etherate (12 mmol) were added thereto, and then refluxed for 24 hours. After completion of the reaction, the reaction mixture was extracted with MC, and column-purified under the conditions of gradient hexane: MC=7:3, which was precipitated in methanol to give Intermediate Compound 3-B as a white powder (yield: 85%).

[Reaction Scheme 3]

(3) Synthesis of Compound 3

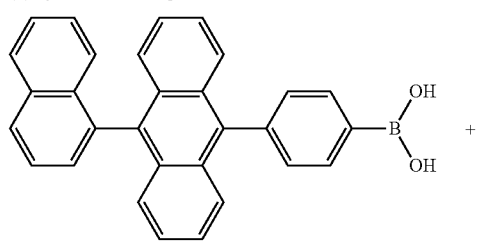

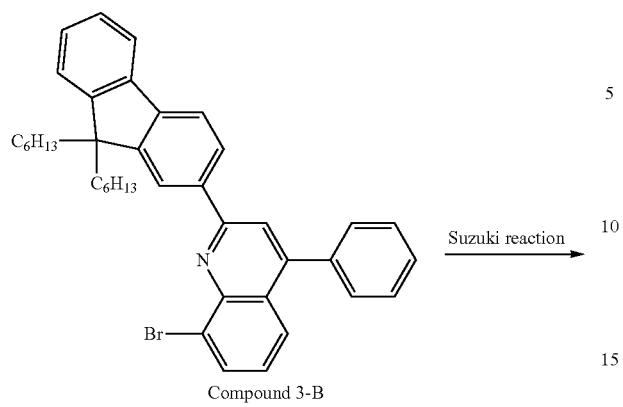

Compound 3-B

Suzuki reaction →

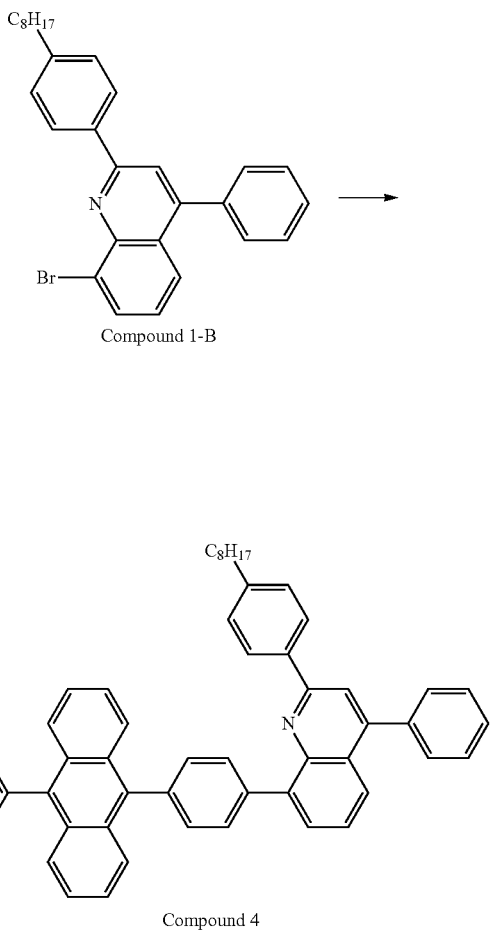

Compound 1-B

Compound 3

Compound 4

4-(10-(Naphthalen-1-yl)anthracen-9-yl)phenyl boric acid (4.5 mmol), Compound 3-B (3 mmol) and Pd(pph$_3$)$_4$ (0.15 mmol) were dissolved in toluene (100 mL). K$_2$CO$_3$ aqueous solution (30 mmol/20 ml water) was added thereto and refluxed. After completion of the reaction, the reaction mixture was extracted with MC, and column-purified under the conditions of gradient hexane:MC=7:3, which was precipitated in methanol to give Compound 3 as a white powder (yield: 80%). The LCMS results of Compound 3 is shown in FIG. 5, and the TGA measurement graph is shown in FIG. 6.

Example 4: Synthesis of Compound 4

(1) Synthesis of Compound 4

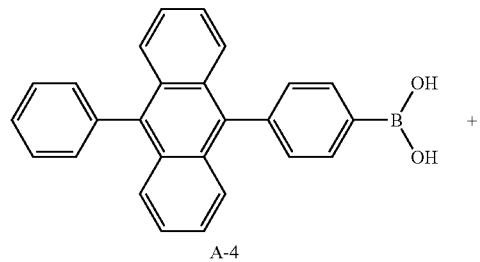

A-4

Compound A-4 (4.5 mmol) and Intermediate Compound 1-B (3 mmol) synthesized according to Reaction Scheme 1-B, and Pd(pph$_3$)$_4$ (0.15 mmol) were dissolved in toluene (100 mL). K$_2$CO$_3$ aqueous solution (30 mmol/20 ml water) was added thereto and refluxed. After completion of the reaction, the reaction mixture was extracted with MC, and column-purified under the conditions of gradient hexane:MC=7:3, which was precipitated in methanol to give Compound 4 as a white powder (yield: 80%).

MS[M+H]+=722, PLmax=420 nm

Example 5: Synthesis of Compound 5

(1) Synthesis of Compound 5

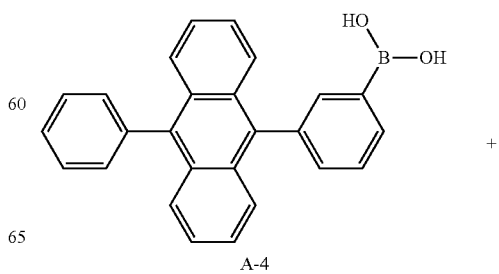

A-4

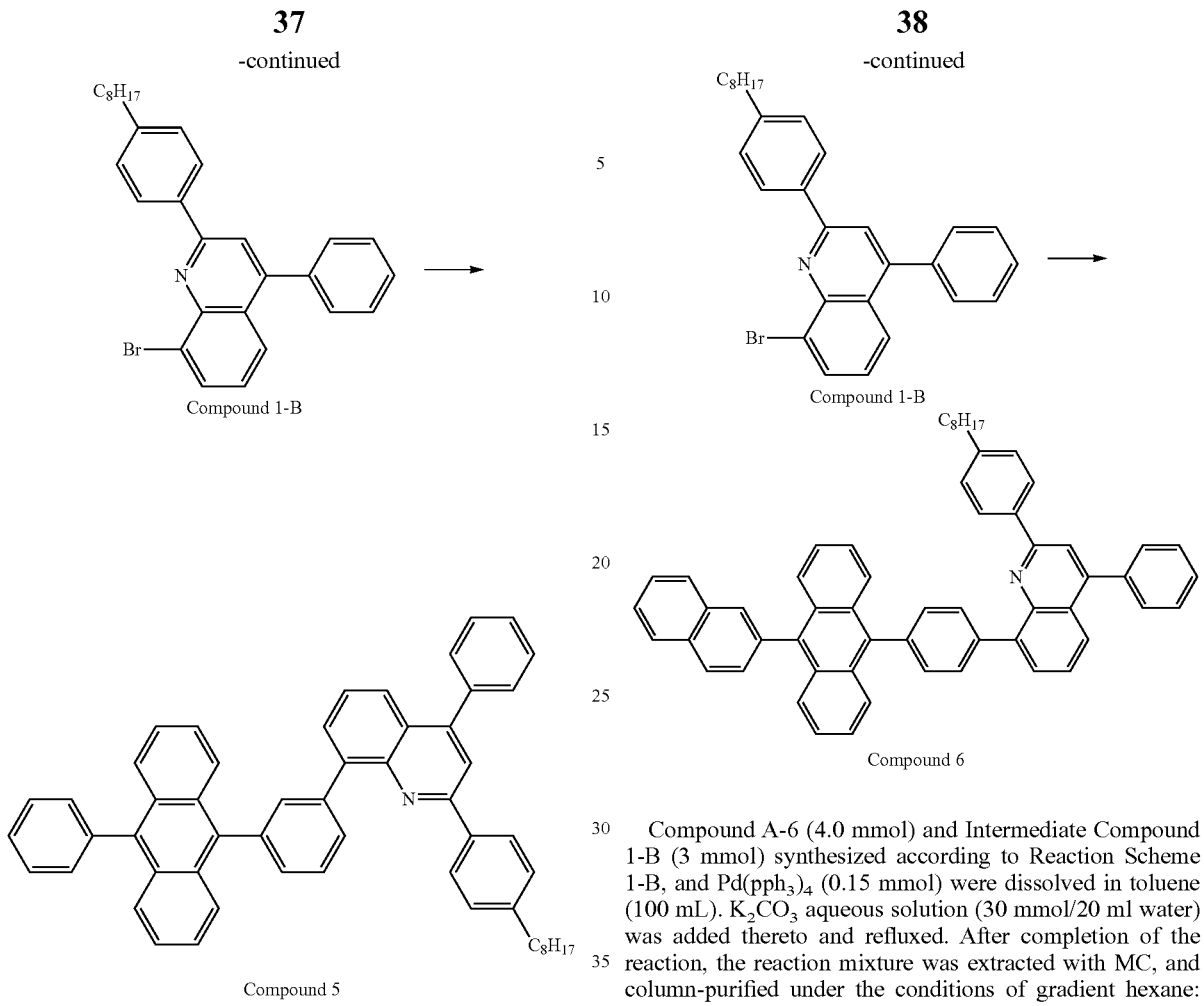

Compound 1-B

Compound 5

Compound 1-B

Compound 6

Compound A-5 (4.0 mmol) and Intermediate Compound 1-B (3 mmol) synthesized according to Reaction Scheme 1-B, and Pd(pph$_3$)$_4$ (0.15 mmol) were dissolved in toluene (100 mL). K$_2$CO$_3$ aqueous solution (30 mmol/20 ml water) was added thereto and refluxed. After completion of the reaction, the reaction mixture was extracted with MC, and column-purified under the conditions of gradient hexane: MC=8:2, which was precipitated in methanol to give Compound 5 as a white powder (yield: 60%).

MS[M+H]+=722

Example 6: Synthesis of Compound 6

(1) Synthesis of Compound 6

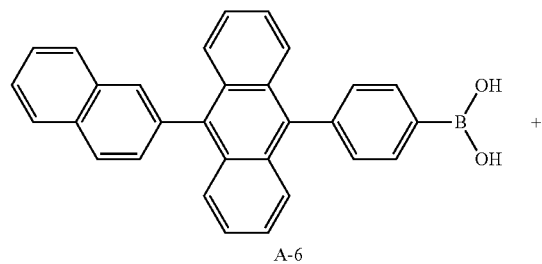

A-6

Compound A-6 (4.0 mmol) and Intermediate Compound 1-B (3 mmol) synthesized according to Reaction Scheme 1-B, and Pd(pph$_3$)$_4$ (0.15 mmol) were dissolved in toluene (100 mL). K$_2$CO$_3$ aqueous solution (30 mmol/20 ml water) was added thereto and refluxed. After completion of the reaction, the reaction mixture was extracted with MC, and column-purified under the conditions of gradient hexane: MC=7:3, which was precipitated in methanol to give Compound 6 as a white powder (yield: 82%).

MS[M+H]+=722

Experimental Example 1: Evaluation of Characteristics of Organic Light Emitting Device A glass substrate on which ITO (indium tin oxide) was coated as a thin film to a thickness of 50 nm was put into distilled water in which a detergent was dissolved, and ultrasonically cleaned. At this time, a product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. In addition, the substrate was cleaned for 5 minutes using oxygen plasma and then transferred to a vacuum depositor.

AI4083 (PEDOT/PSS polymer, CLEVIOS™ P VP AI 4083 from Heraeus Precious Metals GmbH & Co. KG) was spin coated onto the ITO transparent electrode prepared above at 1000 rpm for 60 seconds, baked at 80° C. for 2 minutes, and then baked at 120° C. for 15 minutes to form a hole injection and transport layer with a thickness of 60 nm. A mixed solution of the host compound 1 prepared above and the following BD1 compound in a weight ratio of 94:6 was spin coated onto the hole injection and transport layer and treated at room temperature under $10^{-6}$ torr for 30 minutes using a vacuum chamber to form a light emitting layer with a thickness of 55 nm. This was dried at 130° C. for 10 minutes under a nitrogen gas atmosphere, and then lithium fluoride (LiF) was deposited to a film thickness of about 1 nm, and finally, aluminum was deposited to a thickness of 100 nm to form a cathode.

[BD1]

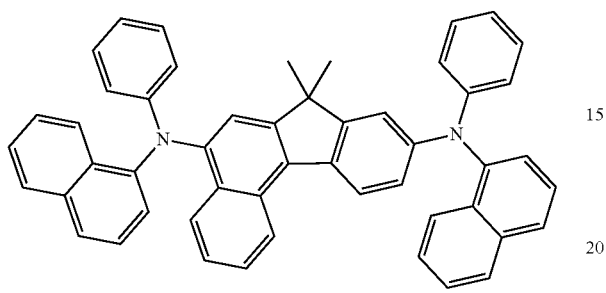

Device structure: ITO (50 nm)/AI4083 (60 nm)/EML (55 nm)/LiF (1 nm)/Al (100 nm)

In the above-mentioned process, the deposition rate of lithium fluoride of the cathode was maintained at 0.3 Å/sec, the deposition rate of aluminum was maintained at 2 Å/sec, and the degree of vacuum during the deposition was maintained at $2×10^{-7}$ to $5×10^{-6}$ torr, thereby manufacturing the organic light emitting device.

Experimental Examples 2 to 6

An organic light emitting device was manufactured in the same manner as in Experimental Example 1, except that the previously prepared Compounds 2 to 6 were used instead of the host compound 1.

Comparative Experimental Examples 1 to 3

An organic light emitting device was manufactured in the same manner as in Experimental Example 1, except that the following Comparative Compounds 1 to 3 were used instead of the host compound 1.

[Comparative Compound 1]

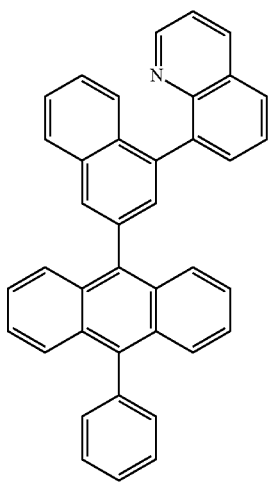

[Comparative Compound 2]

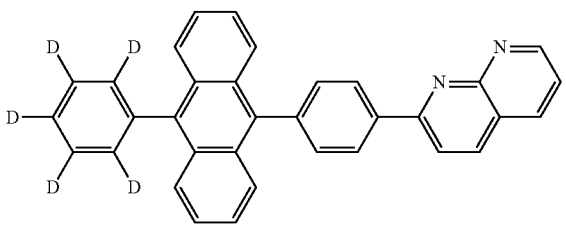

[Comparative Compound 3]

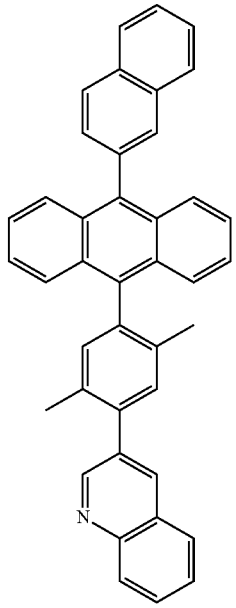

Device Evaluation

The manufactured organic light emitting device was measured for driving voltage, external quantum efficiency (EQE), luminance and lifetime at a current density of 10 mA/cm$^2$, and the results are shown in Table 1 below. The external quantum efficiency was determined by (number of emitted photons)/(number of injected charge carriers).

TABLE 1

| | Light emitting layer host | Driving voltage (V) | Current density (J) | Effi- ciency (Cd/A) | External quantum efficiency (%) |
|---|---|---|---|---|---|
| Experimental Example 1 | Compound 1 | 4.40 | 10 | 6.18 | 8.09 |
| Experimental Example 2 | Compound 2 | 4.46 | 10 | 5.86 | 7.49 |
| Experimental Example 3 | Compound 3 | 4.75 | 10 | 7.43 | 7.86 |
| Experimental Example 4 | Compound 4 | 4.39 | 10 | 4.87 | 6.80 |
| Experimental Example 5 | Compound 5 | 4.67 | 10 | 4.86 | 7.01 |
| Experimental Example 6 | Compound 6 | 4.30 | 10 | 8.31 | 8.49 |
| 비교.Experimental Example 1 | Comparative Compound 1 | 4.66 | 10 | 2.27 | 3.38 |

TABLE 1-continued

| | Light emitting layer host | Driving voltage (V) | Current density (J) | Effi - ciency (Cd/A) | External quantum efficiency (%) |
|---|---|---|---|---|---|
| Comparative Experimental Example 2 | Comparative Compound 2 | 4.38 | 10 | 4.15 | 4.87 |
| Comparative Experimental Example 3 | Comparative Compound 3 | 4.54 | 10 | 4.27 | 4.94 |

As shown in Table 1, it was confirmed that the compounds according to the present disclosure include a characteristic structure, and thus the efficiency is improved as compared with the compounds not containing it. In addition, the compounds according to the present disclosure have excellent solubility in an organic solvent, which facilitates the preparation of a coating composition. From the results of Table 1, it was confirmed that a uniform coating layer can be formed using the above coating composition and the stability of the film was also excellent, and thus the organic light emitting device exhibited more excellent performance.

DESCRIPTION OF SYMBOLS

1: substrate
2: anode
3: light emitting layer
4: cathode
5: hole injection layer
6: hole transport layer
7: light emitting layer
8: electron transport layer

What is claimed is:

1. A compound represented by the following Chemical Formula 1:

[Chemical Formula 1]

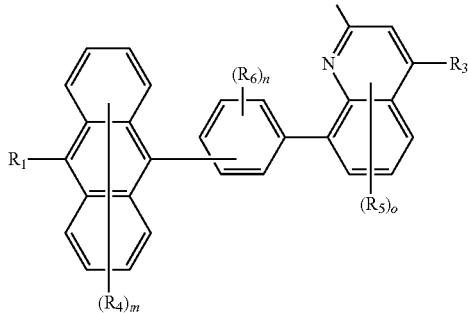

in the Chemical Formula 1,
$R_1$ is a substituted or unsubstituted $C_{6-60}$ aryl,
$R_2$ and $R_3$ are each independently a substituted or unsubstituted $C_{3-10}$ cycloalkyl; a substituted or unsubstituted $C_{6-60}$ aryl; a substituted or unsubstituted $C_{6-60}$ arylamine; or a substituted or unsubstituted $C_{5-60}$ heteroaryl containing one or more hetero atoms selected from the group consisting of N, O, S and Si; or —Si($A_1$)($A_2$)($A_3$), wherein $A_1$, $A_2$ and $A_3$ are each independently a substituted or unsubstituted $C_{1-60}$ alkyl; a substituted or unsubstituted $C_{3-10}$ cycloalkyl; a substituted or unsubstituted $C_{6-60}$ aryl; a substituted or unsubstituted $C_{5-60}$ heteroaryl containing one or more hetero atoms selected from the group consisting of N, O, S and Si; a monovalent non-aromatic condensed polycyclic group; or a monovalent non-aromatic hetero-condensed polycyclic group,
$R_4$ and $R_5$ are each independently hydrogen; deuterium; halogen; or a substituted or unsubstituted $C_{1-60}$ alkyl,
$R_6$ is hydrogen; or deuterium,
m and o are each independently an integer of 0 to 3, and
n is an integer of 0 to 4.

2. The compound of claim 1,
wherein the compound represented by Chemical Formula 1 is a compound represented by the following Chemical Formula 2 or Chemical Formula 3:

[Chemical Formula 2]

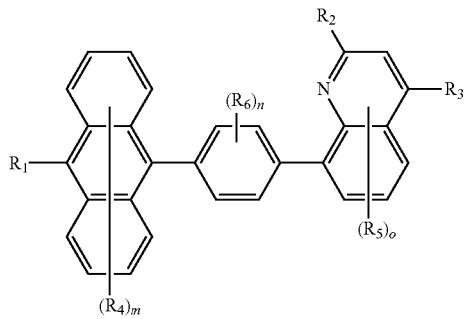

[Chemical Formula 3]

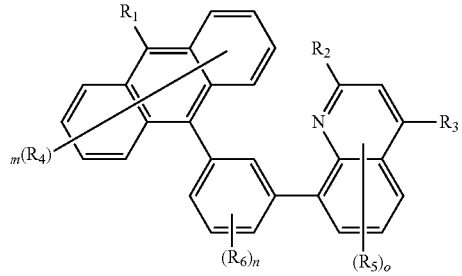

wherein, $R_1$, $R_2$, $R_3$, $R_4$, $R_5$, $R_6$, m, n and o are as defined in claim 1.

3. The compound of claim 1,
wherein $R_1$ is phenyl; biphenylyl; terphenylyl; quarterphenylyl; naphthyl; phenanthrenyl; chrysenyl; fluoranthenyl; pyrenyl; or triphenylenyl.

4. The compound of claim 1,
wherein $R_2$ and $R_3$ are each independently any one selected from the group consisting of:

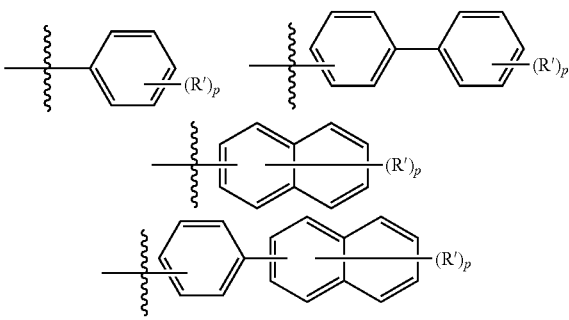

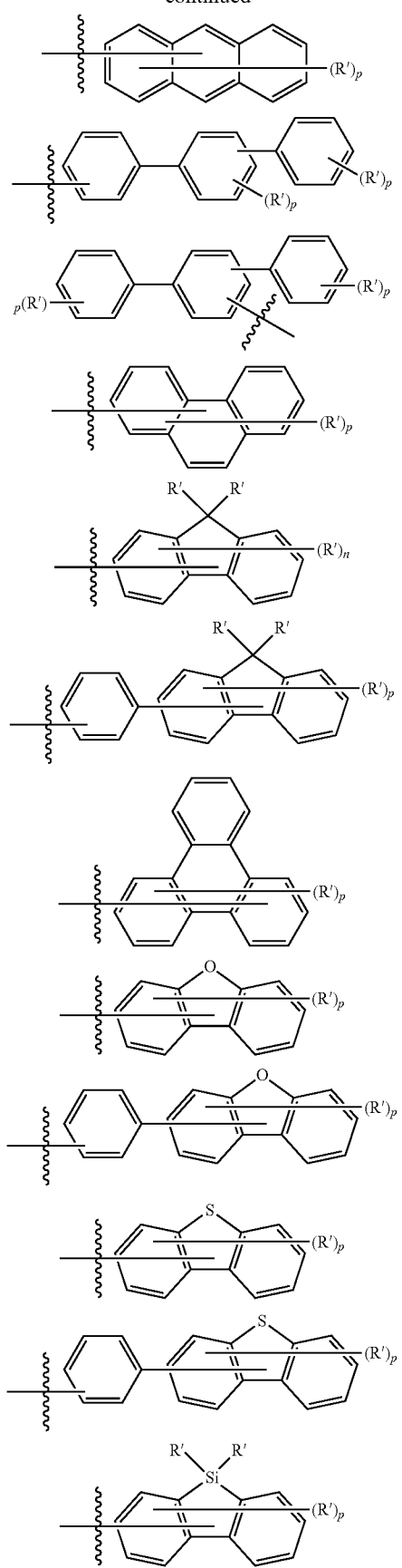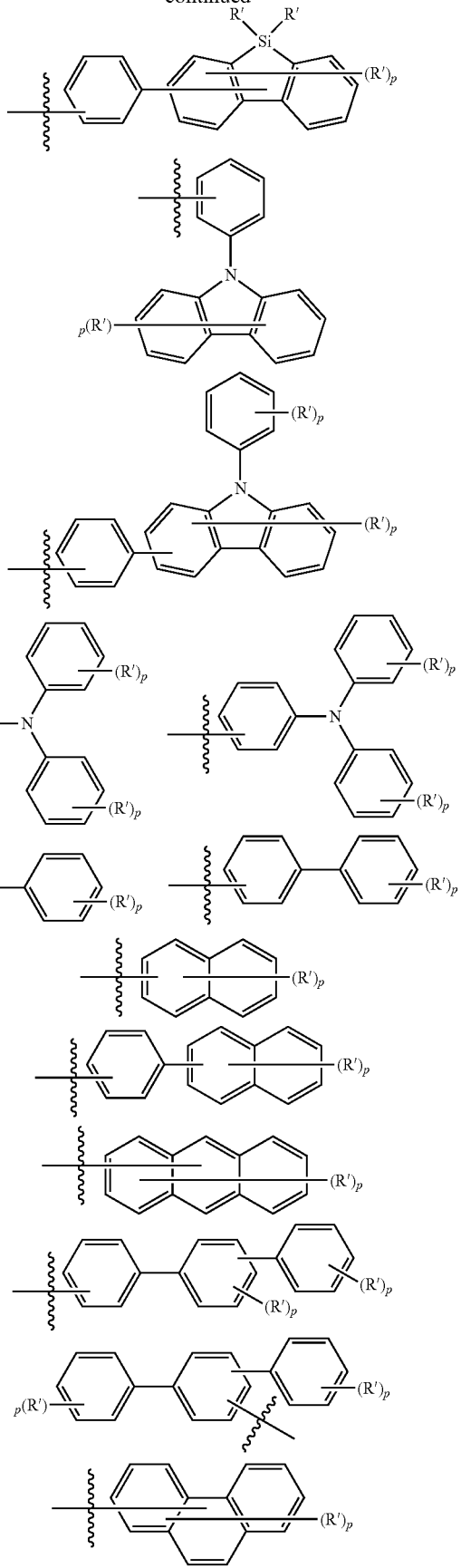

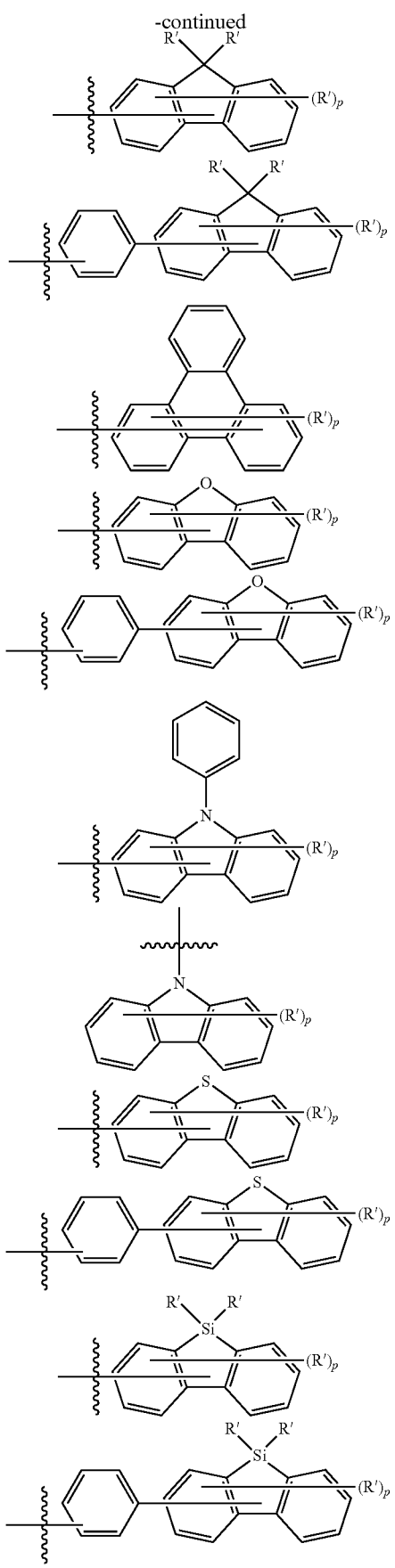
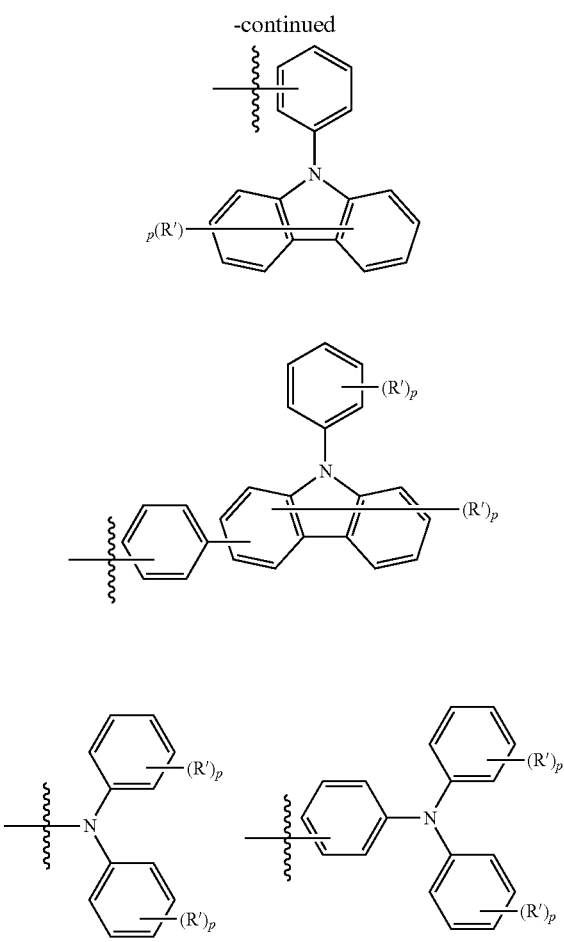

wherein,

R' are each independently hydrogen; deuterium; halogen; or a substituted or unsubstituted $C_{1-60}$ alkyl, and each p is independently an integer of 0 to 3.

5. The compound of claim 4,

R' is hydrogen; or $C_{1-10}$ alkyl.

6. The compound of claim 1, wherein $R_4$ and $R_5$ are each independently hydrogen; deuterium; methyl; ethyl; propyl; n-propyl; isopropyl; butyl; n-butyl; isobutyl; or tert-butyl.

7. The compound of claim 1, wherein the compound represented by Chemical Formula 1 is any one selected from the group consisting of:

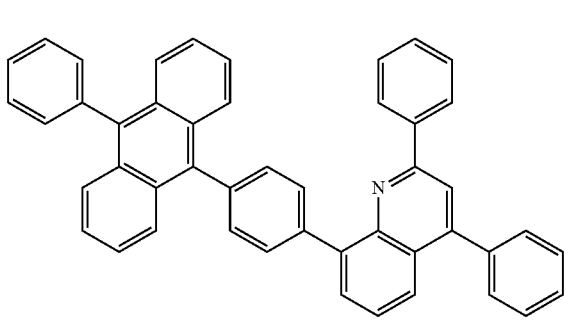

47
-continued
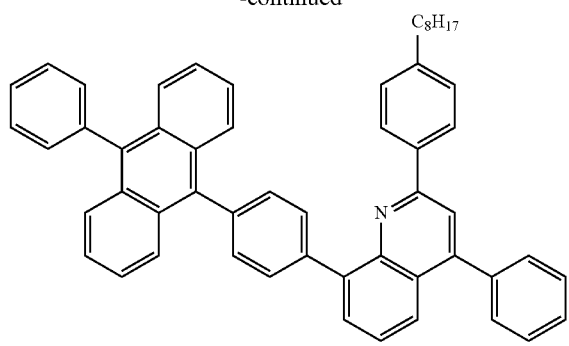
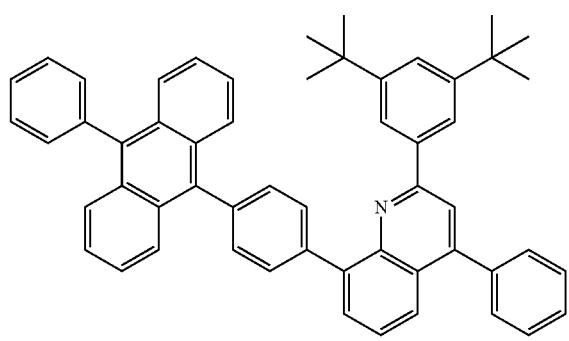
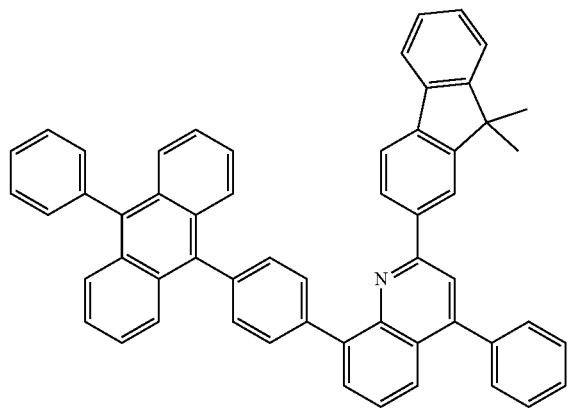
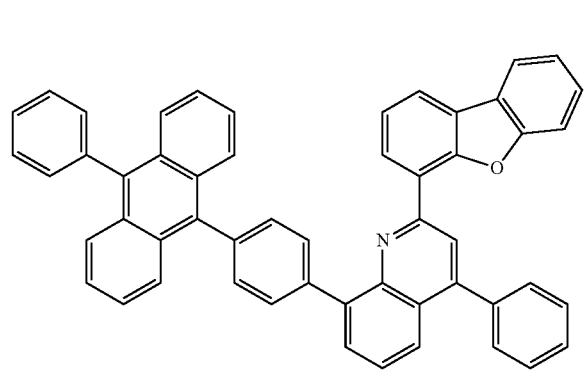
48
-continued
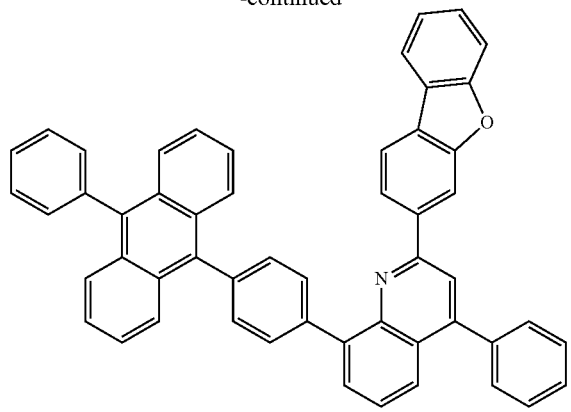
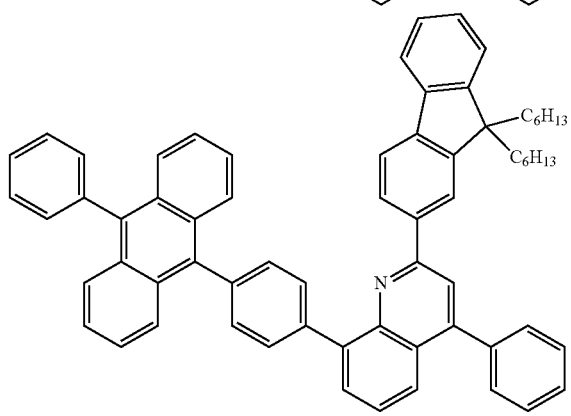
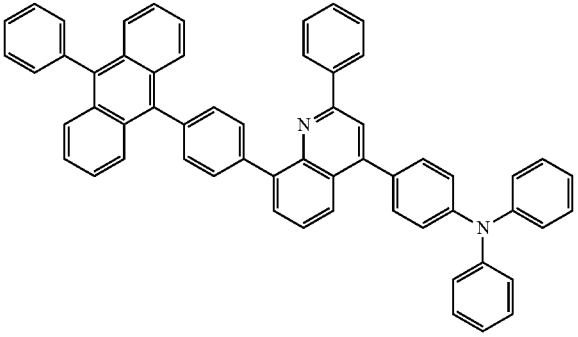
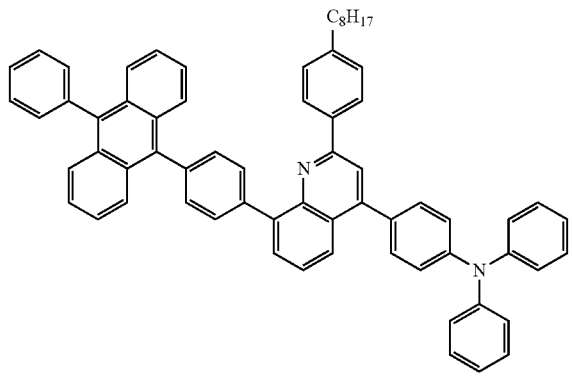

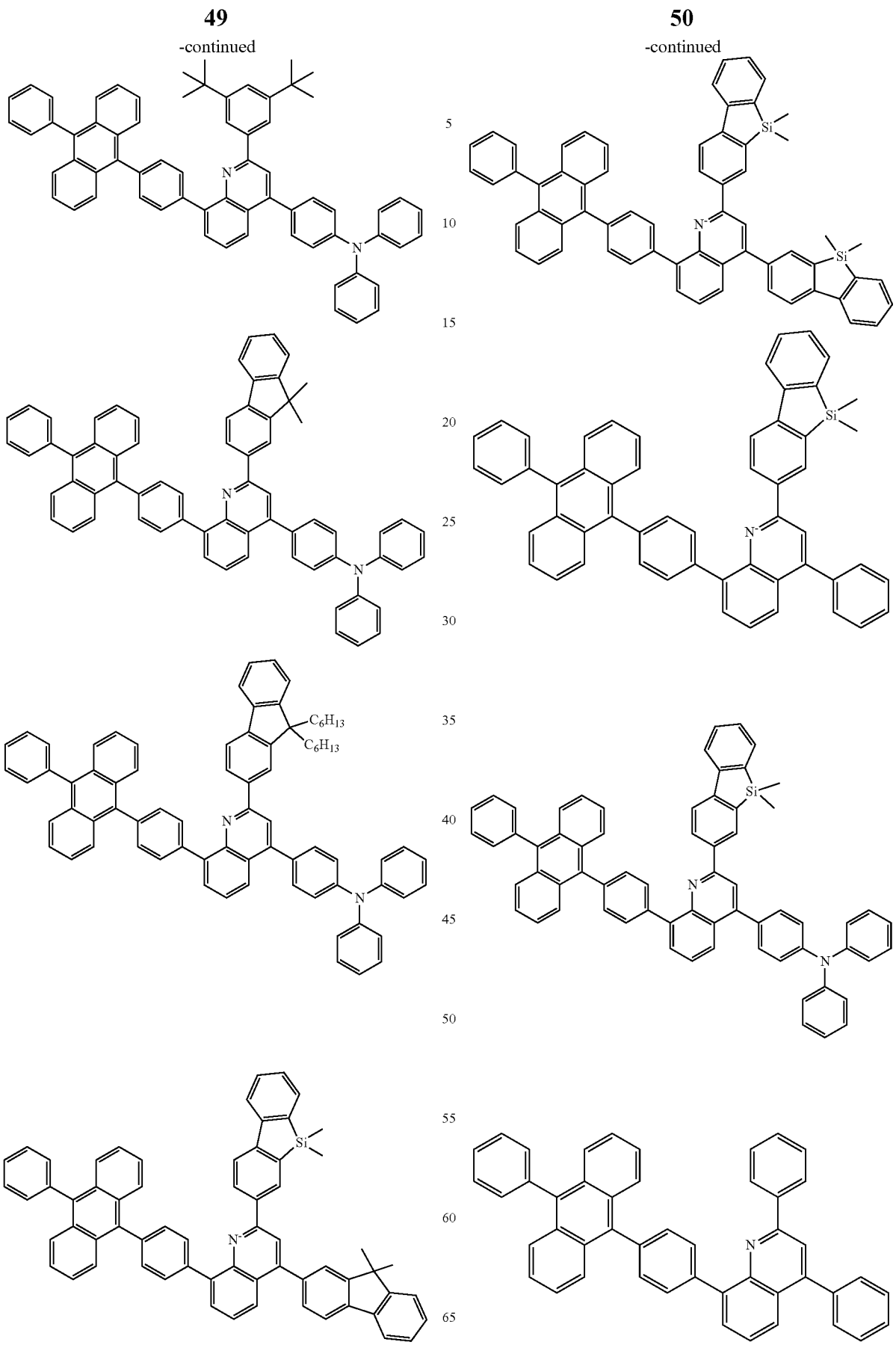

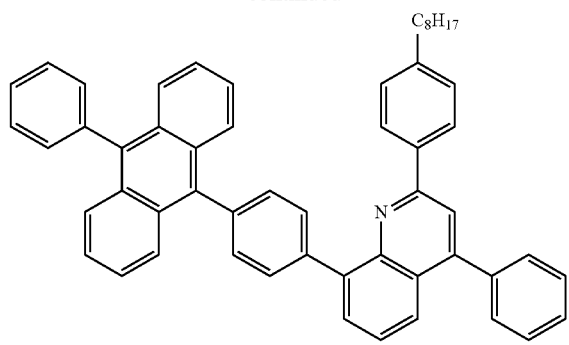
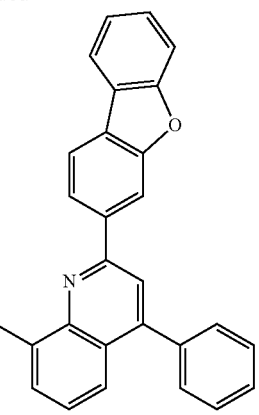
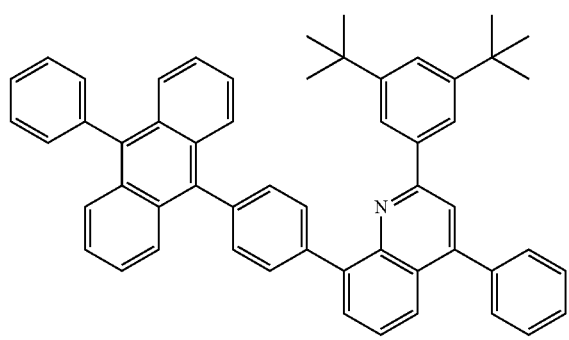
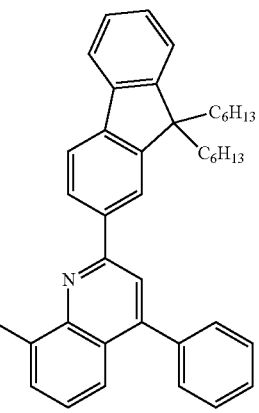
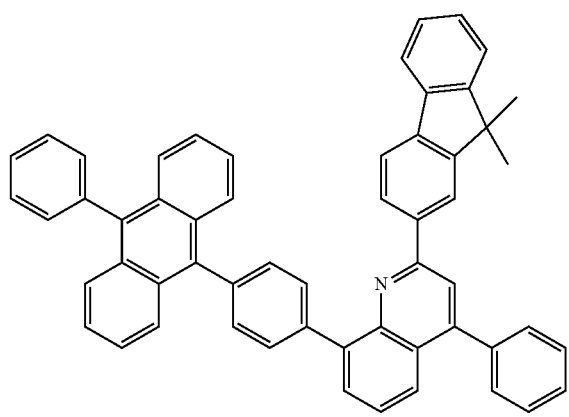
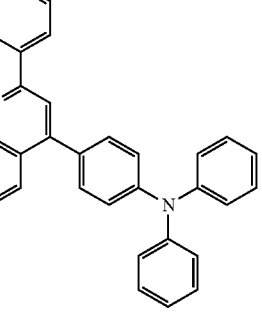
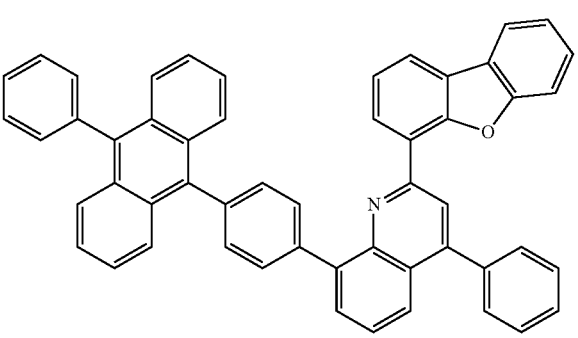
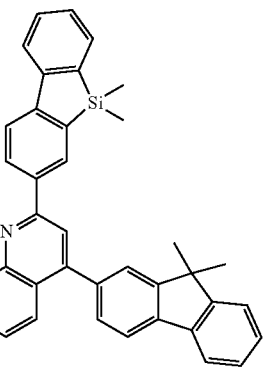

-continued
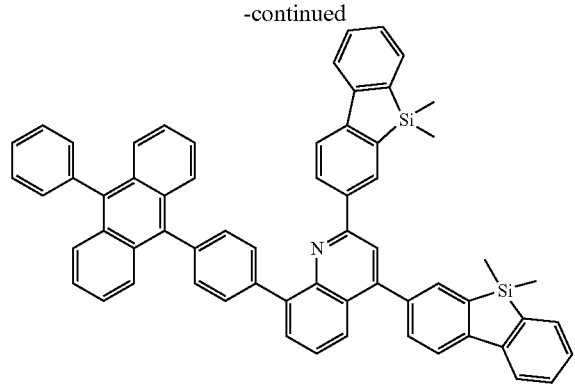
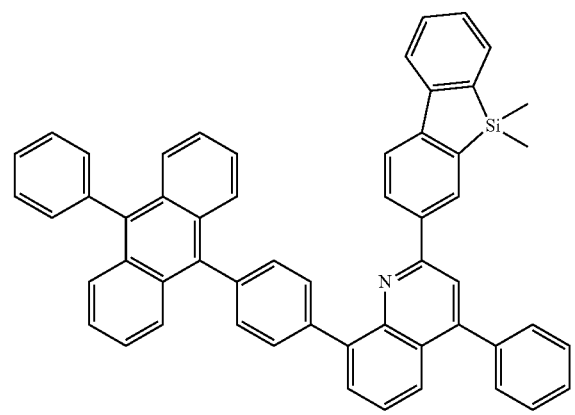
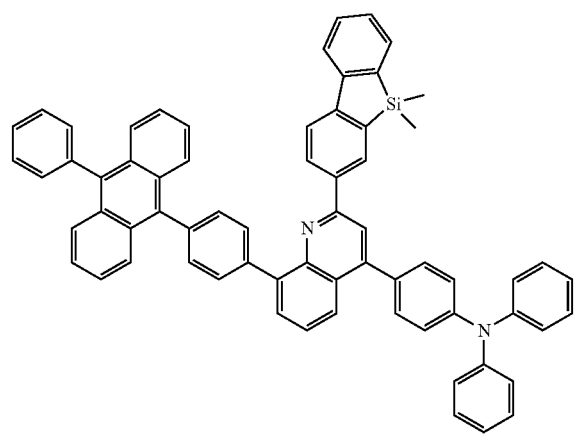
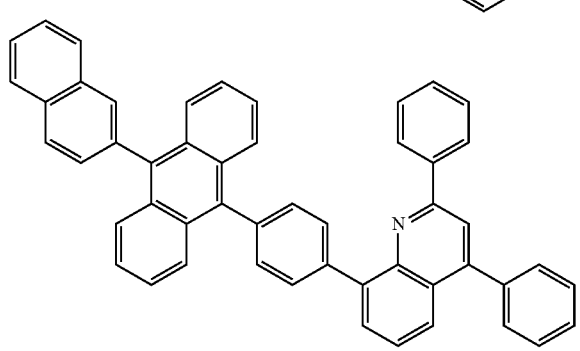
-continued
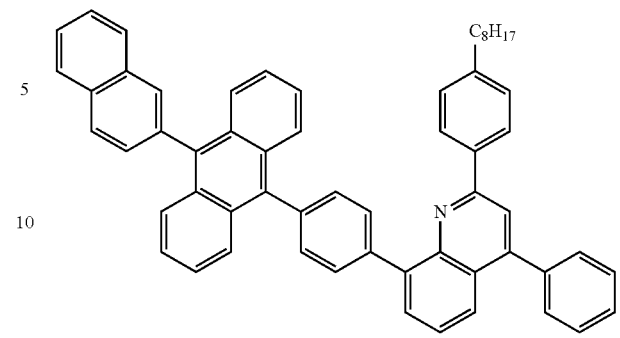
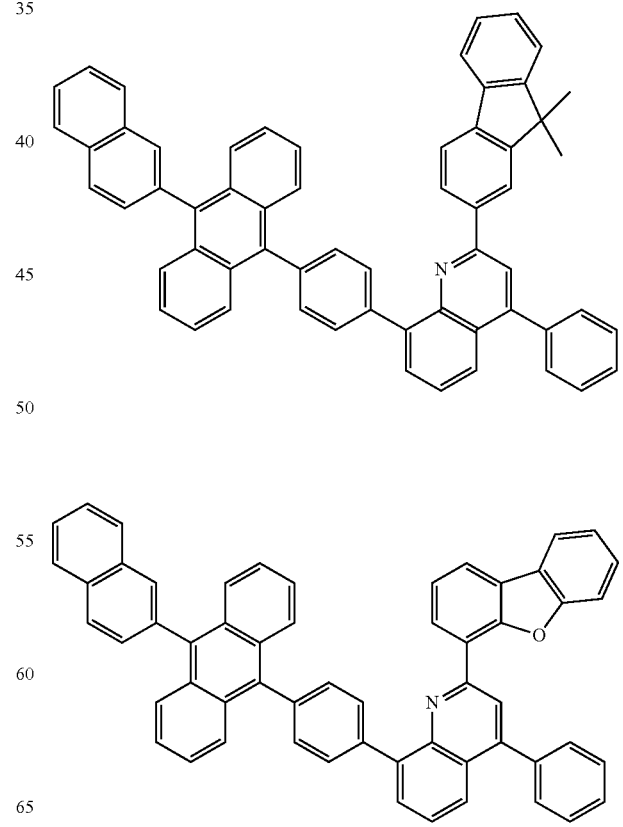

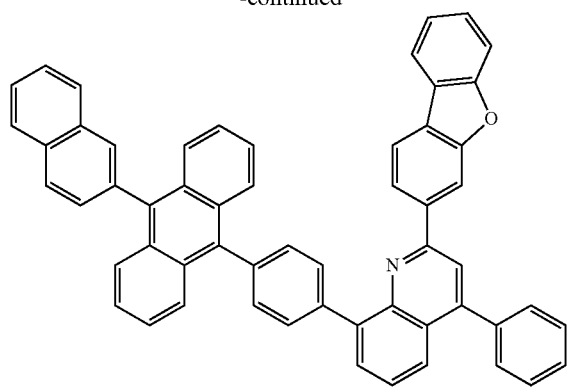
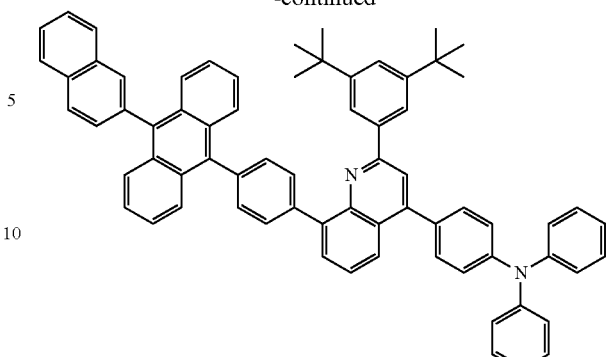
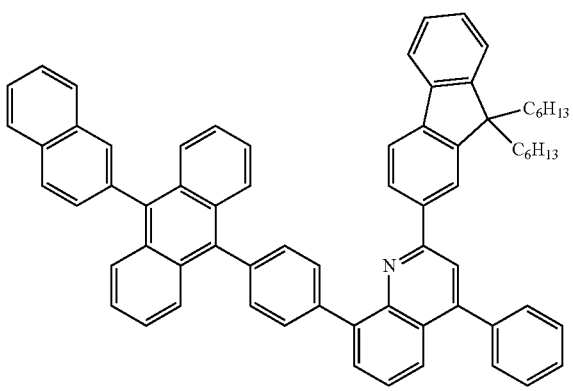
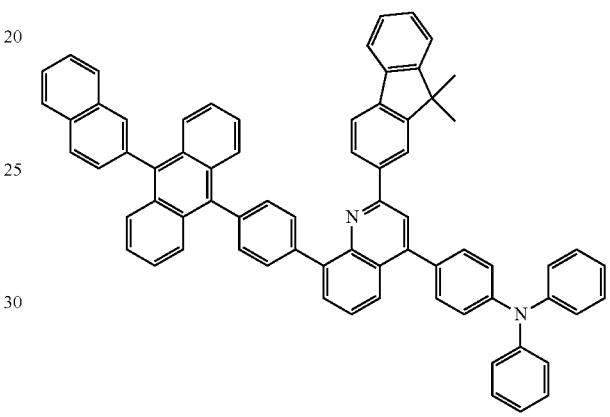
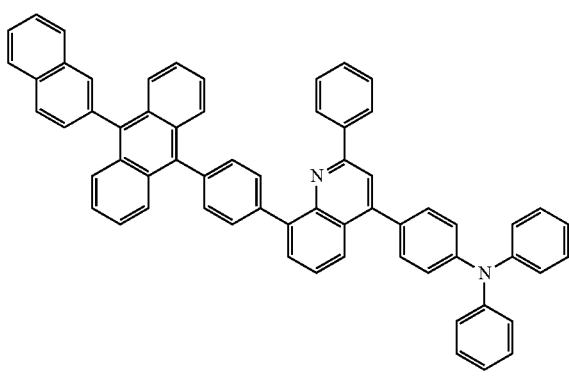
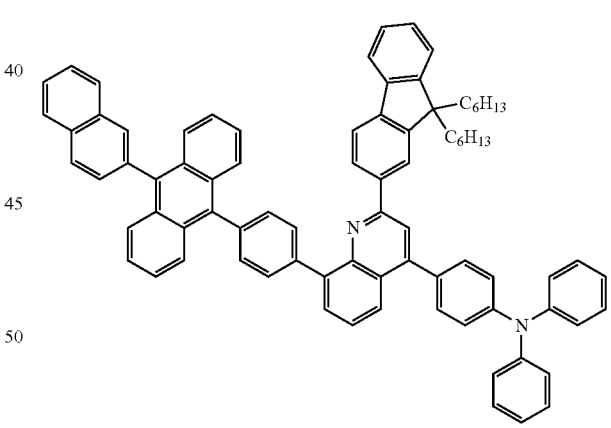
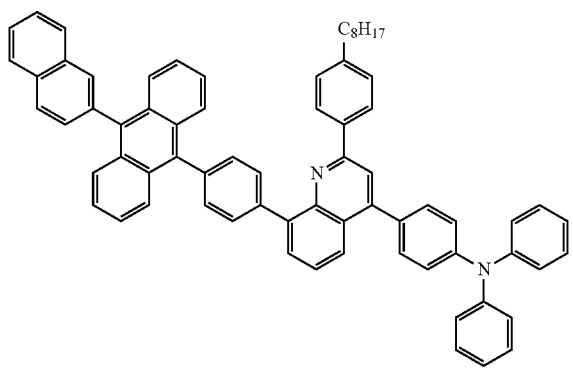
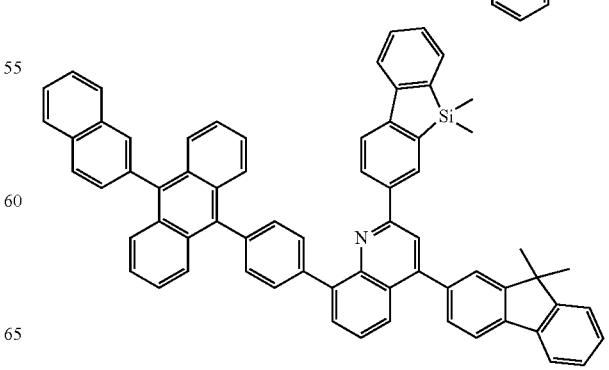

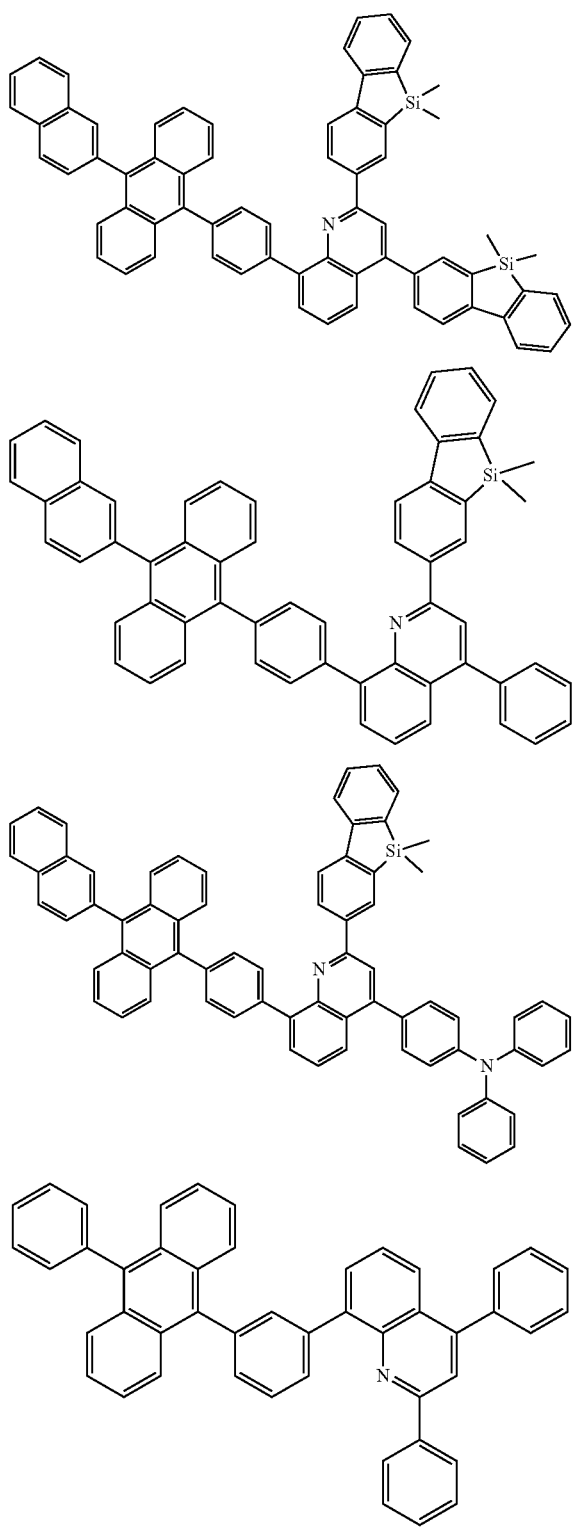
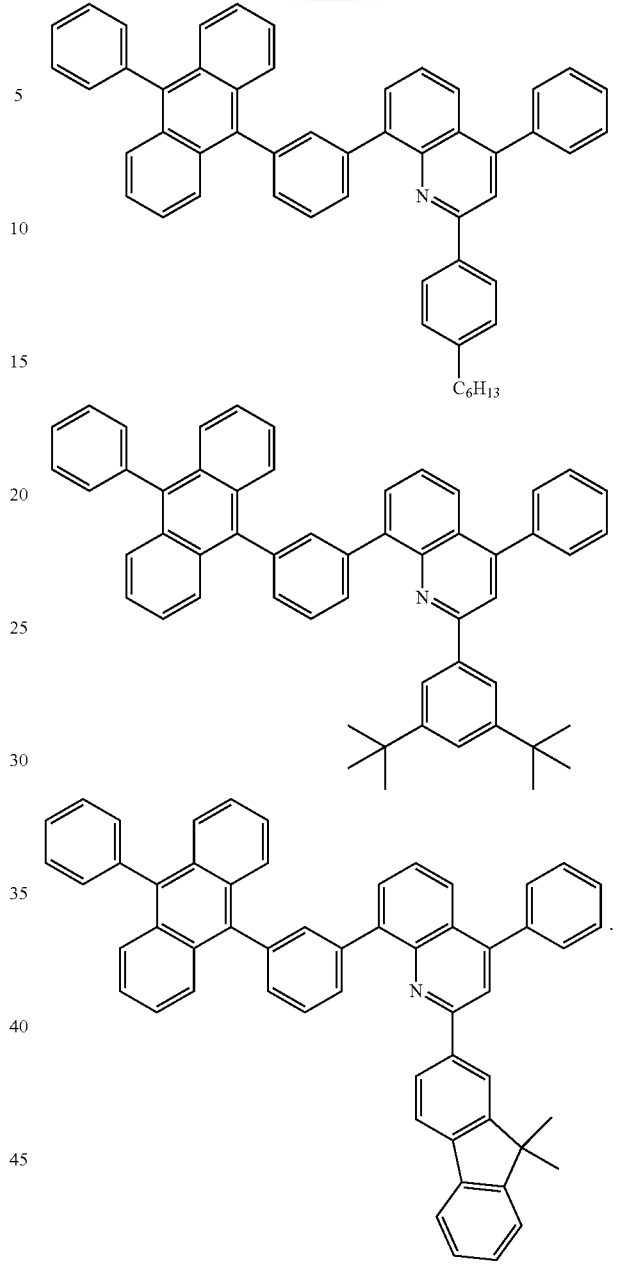

8. An organic light emitting device comprising: a first electrode; a second electrode that is provided opposite to the first electrode; and one or more organic material layers that are provided between the first electrode and the second electrode, wherein at least one layer of the organic material layers includes the compound according to claim 1.

9. The organic light emitting device of claim 8, wherein the at least one layer of the organic material layers including the compound is a light emitting layer.

* * * * *